(12) United States Patent
Will et al.

(10) Patent No.: US 6,399,348 B1
(45) Date of Patent: *Jun. 4, 2002

(54) DNA SEQUENCES FOR MATRIX METALLOPROTEASES, THEIR PRODUCTION AND USE

(75) Inventors: Horst Will; Bernd Hinzmann, both of Berlin (DE)

(73) Assignee: Max-Delbrueck Centrum fuer Molekulare Medizin, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/521,220

(22) Filed: Mar. 8, 2000

Related U.S. Application Data

(63) Continuation of application No. 08/704,711, filed as application No. PCT/DE95/00357 on Mar. 17, 1995, now Pat. No. 6,114,159.

(30) Foreign Application Priority Data

Mar. 17, 1994 (DE) .......................... 44 09 663
Oct. 21, 1994 (DE) .......................... 44 38 838

(51) Int. Cl.$^7$ .......................... C07H 21/04; C12N 9/50
(52) U.S. Cl. .......................... 435/219; 435/226; 435/325; 435/252.3; 435/252.33; 435/254.11; 435/320.1; 536/23.2; 536/23.5
(58) Field of Search .......................... 435/219, 226, 435/325, 252.33, 320.1, 254.11; 536/23.2, 23.5

(56) References Cited

U.S. PATENT DOCUMENTS 6,184,002 B1 * 2/2001 Seiki et al. .................. 435/226

FOREIGN PATENT DOCUMENTS

EP          A 0 685 557     12/1995
WO          WO 95/15374   * 8/1995

OTHER PUBLICATIONS

Bassett, et al., "A Novel Metalloproteinase Gene Specifically Expressed in Stromal Cells of Breast Carcinoma", Nature, 348, 699–704 (1990).

Matrisian et al., The Matrix–Degrading Metalloproteinase, BioEssays, 14:7, 455–463 (1992).

Sato, et al., A Matrix Metalloproteinase Expressed on the Surface of Invasive Tumour Cells, Nature, 370, 61–65 (1994).

Will, et al., "cDNA Sequence and mRNA tissue distribution of a novel human Matrix Metalloproteinase with a potential transmembrane segment", Eur. J. Biochem., 231:3, 602–608 (1995).

* cited by examiner

Primary Examiner—Nashaat T. Nashed
(74) Attorney, Agent, or Firm—Heller Ehrman White and McAuliffe

(57) ABSTRACT

DNA sequences for human matrix metalloproteases are disclosed, as well as homologous DNA sequences homologous and derived therefrom. Also disclosed are the proteins and protein variants coded by these DNA sequences, there expression, preparation and use. The invention has applications in the fields of biomolecular, medical and pharmaceutical research, for medical diagnosis and therapy, and in the pharmaceutical and biotechnological industry.

17 Claims, 10 Drawing Sheets

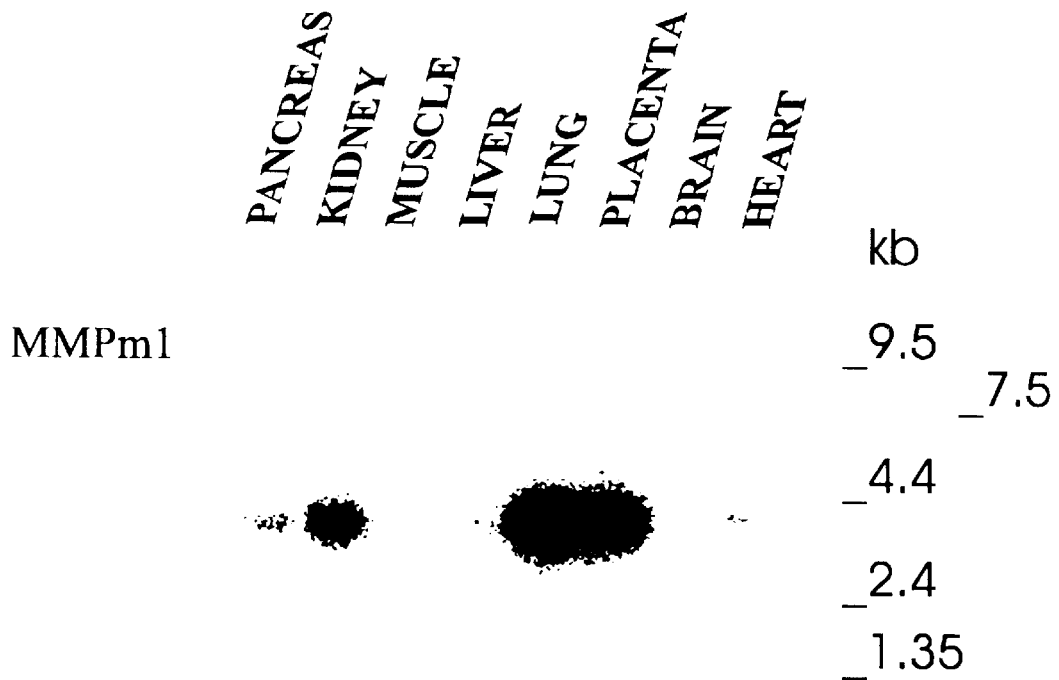
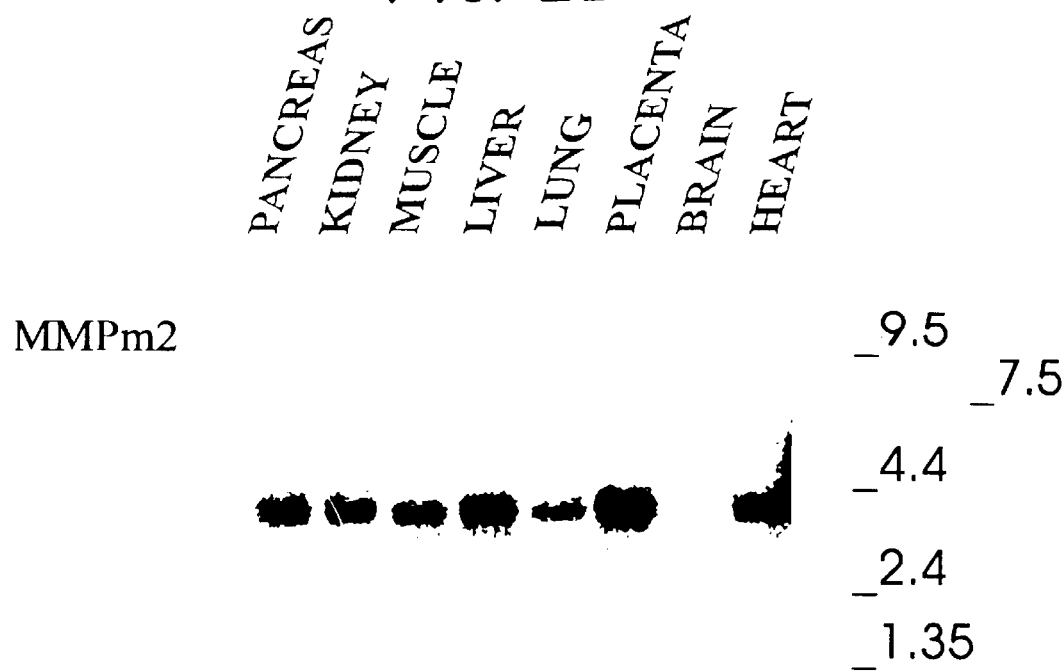

FIG. 3A

```
                          10         20         30         40         50         60
                          .          .          .          .          .          .
MMPm1a.pep    MTYEMEHLFR------CLFA-----ACVSSLV--FGSFFN---------HVVSFS--------
MMPm1b.pep    MS-PAPRPPR------CLL------LPLLT--LGTALASLG---SAQSSSFS-PEAWLQQ
MMPm2.pep     MGSDPSAPGRPGWTGSLLGDREEAARPRLLPLLVLLGCLGLGVAAEDAEVH-AENWLRL
hscollr.pep   M--HSFPPL-------LLLLFWGVVS----------HSFPATLETQEQDV--DLVQKYLEK
hsc1gna.pep   M--FSLKTL-------PFLLLLHVQIS---------KAFP--VSSKEKNT--KTVQDYLEK
p08253.swisspro M--EALMARGALTGPLR-ALCLLGCLLSHAAAPSPIIKFPGDVAPK-TDKELAVQYLNT
hs4cola.pep   M--------SLWQPLVLVLLVLGCCFAAPRQRQSTLVLFPGDLRTNLTDRQLAEEYLYR
hsmmp3a.pep   M-------KSL-----PILLLLCVAVC---------SAYPLDGAARGEDTSMNLVQKYLEN
hsstrom2.pep  M-------MHL-----AFLVLLCLPVC---------SAYPLSGAAKEEDSNKDLAQQYLEK
hsstrol3.pep  MA--------PAAWL------RSAAARALLPPMLLLLQPPPLLARA-----------
                                  *

FLFFESLALSSGVECNGAISAYCNLCLLGSSDSPASASQIAGKADADTMKAMRRPRCGVP
MMPm1a.pep                YGYLPPGDLRTHTQRSPQ-------SLSAAIAAMQKFYGLQVTGKADADTMKAMRRPRCGVP
MMPm1b.pep                YGYLPQPSRHMSTMRSAQI------LASALAEMQRFYGIPVTGVLDEETKEWMKRPRCGVP
MMPm2.pep                 Y-YNLKNDGRQVEKRRNSGP-----VVEKLKQMQEFFGLKVTGKPDAETLKVMKQPRCGVP
hscollr.pep               F-YQLPSNQYQSTRKNGTNV-----IVEKLKEMQRFFGLNVTGKPNEETLDMMKKPRCGVP
hsc1gna.pep               F-YGCPKE-------SCNLFV----LKDTLKKMQKFFGLPQTGDLDQNTIETMRKPRCGNP
p08253.swisspro           YGYTRVAEM------RGESKS----LGPALLLLQKQLSLPETGELDSATLKAMRTPRCGVP
hs4cola.pep               Y-YDLEKDVKQFVRRKDSGP-----VVKKIREMQKFLGLEVTGKLDSDTLEVMRKPRCGVP
hsmmp3a.pep               Y-YNLEKDVKQF-RRKDSNL-----IVKKIQGMQKFLGLEVTGKLDTDTLEVMRKPRCGVP
hsstrom2.pep              ---LPPDVHHILHAERRGPQPWHAALPSSPAPAP-------ATQEAPRPASSLRPPRCGVP
hsstrol3.pep                           +                     +    +   +      ++     +  +  *   ** *
```

FIG. 3B

```
MMPm1a.pep       DKFGAEIKANV--RRKRYAIQGLKWQHNEITFCIQNYTPKVGEYATYEAIRKAFRVWESA
MMPm1b.pep       DKFGAEIKANV--RRKRYAIQGLKWQHNEITFCIQNYTPKVGEYATYEAIRKAFRVWESA
MMPm2.pep        DQFGVRVKANLRRRRRKRYALTGRKWNNHHLTFSIQNYTEKLGWYHSMEAVRRAFRVWEQA
hscollr.pep      DVAQFVLTEGNP-------------RWEQTHLTYRIENYTPDLPRADVHAIEKAFQLWSNV
hsclgna.pep      DSGGFMLTPGNP-------------KWERTNLTYRIRNYTPQLSEAFVERAIKDAFELWSVA
p08253.swisspro  DVANYNFFPRKP-------------KWDKNQITYRIIGYTPDLDPETVDDAFARAFQVWSDV
hs4cola.pep      DLGRFQTFEGDL-------------KWHHHNITYWIQNYSEDLPRAVIDDAFARAFALWSAV
hsmmp3a.pep      DVGHFRIFPGIP-------------KWRKTHLTYRIVNYTPDLPKDAVDSAVEKALKVWEEV
hsstrom2.pep     DVGHFSSFPGMP-------------KWRKTHLTYRIVNYTPDLPRDAVDSAIEKALKVWEEV
hsstrol3.pep     DPSDG---LSARNRQKRFVLSGGRWEKTDLTYRILRFPWQLVQEQVRQTMAEALKVWSDV
                 *               +     * * +++++  *   +      + + +   + +++

MMPm1a.pep       TPLRFREVPYAYIREGHEKQADIMIFFAEGFHGDSTPFDGEGGFLAHAYFPGPNIGGDTH
MMPm1b.pep       TPLRFREVPYAYIREGHEKQADIMIFFAEGFHGDSTPFDGEGGFLAHAYFPGPNIGGDTH
MMPm2.pep        TPLVFQEVPYEDIRLRRQKEADIMVLFASGFHGDSSPFDGTGGFLAHAYFPGPGLGGDTH
hscollr.pep      TPLTFTKV-------SEGQADIMISFVRGDHRDNSPFDGPGPGNLAHAFQPGPGIGGDAH
hsclgna.pep      SPLIFTRI-------SQGEADINIAFYQRDHGDNSPFDGPGPNGILAHAFQPGQGIGGDAH
p08253.swisspro  TPLRFSRI-------HDGEADIMINFGRWEHGDGYPFDGKDGLLAHAFAPGTGVGGDSH
hs4cola.pep      TPLTFTRV-------YSRDADIVIQFGVAEHGDGYPFDGKDGLLAHAFPPGPGIQGDAH
hsmmp3a.pep      TPLTFSRL-------YEGEADIMISFAVREHGDFYPFDGPGNVLAHAYAPGPGINGDAH
hsstrom2.pep     TPLTFSRL-------YEGEADIMISFAVKEHGDFYSFDGPGHSLAHAYPPGPGLYGDIH
hsstrol3.pep     TPLTFTEV-------HEGRADIMIDFARYWDGDLPFDGPGGILAHAFFPKTHREGDVH
                 ***  *          *  *** +      *   **     ***+    +      *
```

FIG. 3C

```
MMPm1a.pep         FDSAEPWTVRNEDL----------------------------------------
MMPm1b.pep         FDSAEPWTVRNEDL----------------------------------------
MMPm2.pep          FDADEPWTFSSTDL----------------------------------------
hscollr.pep        FDEHERWTNNFT------------------------------------------
hsclgna.pep        FDAEETWTNTSA------------------------------------------
p08253.swisspro    FDDDELWTLGEGQVVRVKYGNADGEYCKFPFLFNGKEYNSCTDTGRSDGFLWCSTTYNFE
hs4cola.pep        FDDDELWSLGKGVVVPTRFGNADGAACHFPFIFEGRSYSACTTDGRSDGLPWCSTTANYD
hsmmp3a.pep        FDDDEQWTKDTT------------------------------------------
hsstrom2.pep       FDDDEKWTEDAS------------------------------------------
hsstrol3.pep       FDYDETWTIGDDQ-----------------------------------------
                   **    *  *  *+

MMPm1a.pep         ------------------------------------------------------
MMPm1b.pep         ------------------------------------------------------
MMPm2.pep          ------------------------------------------------------
hscollr.pep        ------------------------------------------------------
hsclgna.pep        ------------------------------------------------------
p08253.swisspro    KDGKYGFCPHEALFTMGGNAEGQPCKFPFRFQGTSYDSCTTEGRTDGYRWCGTTEDYDRD
hs4cola.pep        TDDRFGFCPSERLYTRDGNADGKPCQFPFIFQGQSYSACTTDGRSDGYRWCATTANYDRD
hsmmp3a.pep        ------------------------------------------------------
hsstrom2.pep       ------------------------------------------------------
hsstrol3.pep       ------------------------------------------------------
```

FIG. 3D

```
MMPm1a.pep       ------------------------------------------------
MMPm1b.pep       ------------------------------------------------
MMPm2.pep        ------------------------------------------------
hscollr.pep      ------------------------------------------------
hsclgna.pep      KKYGFCPETAMSTV-GGNSEGAPCVFPFTFLGNKYESCTSAGRSDGKMWCATTANYDDDR
p08253.swisspro  KLFGFCPTRADSTVMGGNSAGELCVFPFTFLGKEYSTCTSEGRGDGRLWCATTSNFDSDK
hs4cola.pep      ------------------------------------------------
hsmmp3a.pep      ------------------------------------------------
hsstrom2.pep     ------------------------------------------------
hsstrol3.pep     ------------------------------------------------

MMPm1a.pep       -------NGNDIFLVAVHELGHALGLEHSSDPSAIMAPFYQ-WMDTENFVLPDDDRRGIQ
MMPm1b.pep       -------NGNDIFLVAVHELGHALGLEHSSDPSAIMAPFYQ-WMDTENFVLPDDDRRGIQ
MMPm2.pep        -------HGNNLFLVAVHELGHALGLEHSSNPNAIMAPFYQ-WKDVDNFKLPEDDLRGIQ
hscollr.pep      -------EYNLHRVAAHELGHSLGLSHSTDIGALMYPSY-TF--SGDVQLAQDDIDGIQ
hsclgna.pep      -------NYNLFLVAAHEFGHSLGLAHSSDPGALMYPNY-AFRETSNYSLPQDDIDGIQ
p08253.swisspro  KWGFCPDQGYSLFLVAAHEFGHAMGLEHSQDPGALMAPIYT-YTK--NFRLSQDDIKGIQ
hs4cola.pep      KWGFCPDQGYSLFLVAAHEFGHALGLDHSSVPEALMYPRE-FTE--GPPLHKDDVNGIR
hsmmp3a.pep      -------GTNLFLVAAHEIGHSLGLFHSANTEALMYPLYHSLITDLTRFRLSQDDINGIQ
hsstrom2.pep     -------GTNLFLVAAHELGHSLGLFHSANTEALMYPLYNSFTELAQFRLSQDDVNGIQ
hsstrol3.pep     -------GTDLLQVAAHEFGHVLGLQHTTAAKALMSAFYT-FRYP--LSLSPDDCRGVQ
                    + ***+****+**+*+++* ***+*+* +  * +* **    *   **  *++
```

FIG. 3E

```
MMPm1a.pep        QLYGGESG--------FPTKMPP--QP-RTTSRPSVPDKPKNPT-----------------
MMPm1b.pep        QLYGGESG--------FPTKMPP--QP-RTTSRPSVPDKPKNPT-----------------
MMPm2.pep         QLYGTPDG----QPQPTQPLPTVTPR--RPGRPDHRPPRPPQPPPGGKPERPPKPGPPV
hscollr.pep       AIYGRSQN-----------------------------------PVQ-------PIGPQTPK
hsclgna.pep       AIYGLSSN-----------------------------------PIQ-------PTGPSTPK
p08253.swisspro   ELYGASPDIDL------------------GTGPT-------PTLGPVTP-----------
hs4cola.pep       HLYGPRPEPEPRPPTTTPQPTAPPTVCPTGPPTVHPSERPTAGPTGPPSAGPTGPPTAG
hsmmp3a.pep       SLYGPPPD-----------------------------------SPETPLVPTEPVPPEPGTPA
hsstrom2.pep      SLYGPPPA-----------------------------------STEEPLVPTKSVPSGSEMPA
hsstrol3.pep      HLYG------------QPWPTVTSR--TPALG------PQAGIDTNEIAP-----L
                   +**                                                           +

MMPm1a.pep        --------------YGPNICDGN--FDTVAMLRGEMFVFKERWFWRVRNNQVMD-GYPMPIGQF
MMPm1b.pep        --------------YGPNICDGN--FDTVAMLRGEMFVFKERWFWRVRNNQVMD-GYPMPIGQF
MMPm2.pep         QPRATERPDQYGPNICDGD--FDTVAMLRGEMFVFKGRWFWRVRHNRVLD-NYPMPIGHF
hscollr.pep       A-------------CDSKLITFDAITTIRGEVMFFKDRFYMR-TNPFYPEVELNF-TSVF
hsclgna.pep       P-------------CDPSLITFDAITTLRGEILFFKDRYFWR-RHPQLQRVEMNF-ISLF
p08253.swisspro   --------------EICKQDIVFDGIAQIRGEIFFFKDRFIWRTVTPRD-KPMGPLLVATF
hs4cola.pep       PSTATTVPLSPVDDACNVNI-FDAIAEIGNQLYLFKDGKYWRFSEGRGSRPQGPFLIADK
hsmmp3a.pep       N-------------CDPALSFDAVSTLRGEILIFKDRHFWR-KSLRKLEPELHL-ISSF
hsstrom2.pep      K-------------CDPALSFDAISTLRGEYLFFKDRYFWR-RSHWNPEPEFHL-ISAF
hsstrol3.pep      EPDAP---------PDACEAS--FDAVSTIRGELFFFKAGFVWRLRGGQLQP-GYPALASRH
                        * *  ****+ ++   **     +
```

FIG. 3F

```
MMPm1a.pep        WRGLPASINTAYER-KDGKFVFFKGDKHWVFDEASLEPGYPKHI-KELGRGLPTDKIDAA
MMPm1b.pep        WRGLPASINTAYER-KDGKFVFFKGDKHWVFDEASLEPGYPKHI-KELGRGLPTDKIDAA
MMPm2.pep         WRGLPGDISAAYER-QDGRFVFFKGDRYWLFREANLEPGYPQPL-TSYGLGIPYDRIDTA
hscollr.pep       WPQLPNGLEAAYEFADRDEVRFFKGNKYWAVQGQNVLHGYPKDIYSSFGFPRTVKHIDAA
hsclgna.pep       WPSLPTGIQAAYEDFDRDLIFLFKGNQYWALSGYDILQGYPKDI-SNYGFPSSVQAIDAA
p08253.swisspro   WPELPEKIDAVYEAPQEEKAVFFAGNEYWIYSASTLERGYPKPL-TSLGLPPDVQRVDAA
hs4cola.pep       WPALPRKLDSVFEEPLSKKLFFFSGRQVWVYTGASVL-G-PRRL-DKLGLGADVAQVTGA
hsmmp3a.pep       WPSLPSGVDAAYEVTSKDLVFIFKGNQFWAIRGNEVRAGYPRGIHT-LGFPPTVRKIDAA
hsstrom2.pep      WPSLPSYLDAAYEVNSRDTVFIFKGNEFWAIRGNEVQAGYPRGIHT-LGFPPTIRKIDAA
hsstrol3.pep      WQGLPSPVDAAFED-AQGHIWFFQGAQYWVYDGEKPVLG-PAPL-TELG--LVRFPVHAA
                  *+  **      +   +++*       +     *   *      +             ++ *

MMPm1a.pep        LFWMPN-GKTYFFRGNKYYRFNEELRAVDSEYPKNIK-VWEGIPESPRGSFMGSDEVFTY
MMPm1b.pep        LFWMPN-GKTYFFRGNKYYRFNEELRAVDSEYPKNIK-VWEGIPESPRGSFMGSDEVFTY
MMPm2.pep         IWWEPT-GHTFFFQEDRYWRFNEETQRGDPGYPKPIS-VWQGIPASPKGAFLSNDAAYTY
hscollr.pep       LS-EENTGKTYFFVANKYWRYDEYKRSMDPGYPKMIAHDFPGIGHKVDAV--FMKDGFFY
hsclgna.pep       VF---YRSKTYFFVNDQFWRYDQFWRYDNQRQFMEPGYPKSISGAFPGIESKVDAV--FQQEHFFH
p08253.swisspro   FN-WSKNKKTYIFAGDKFWRYNEVKKKMDPGFPKLIADAWNAIPDNLDAVVDLQGGHSY
hs4cola.pep       LR-SGRGKM-LLFSGRRLWRFDVKAQMVDPRSASEVDRMFPGVP--LDTHDVFQYREKAY
hsmmp3a.pep       IS-DKEKNKTYFFVEDKYWRFDEKRNSMEPGFPKQIAEDFPGIDSKIDAV--FEEFGFFY
hsstrom2.pep      VS-DKEKKKTYFFAADKYWRFDENSQSMEQGFPRLIADDFPGVEPKVDAV--LQAFGFFY
hsstrol3.pep      LVWGPEKNKIYFFRGRDYWRFHPSTRRVDSPVPRRAT-DWRGVPSEIDAAFQDADG-YAY
                    *+*     ****    +      +* *     +++      +                +
```

FIG. 3G

```
MMPmla.pep         FYKGNKYWKFNNQ-KLKVEPGYPKSALRDWMGC----------PSGGRP----DEGTEEET
MMPmlb.pep         FYKGNKYWKFNNQ-KLKVEPGYPKSALRDWMGC----------PSGGRP----DEGTEEET
MMPm2.pep          FYKGTKYWKFDNE-RLRMEPGYPKSILRDFMGCQEHVEPGPRWPDVARPFNPHGGAEPGA
hscollr.pep        FFHGTRQYKFDPKT--KRILTL--QKANSWFNCRKNx-----------------------
hsclgna.pep        VFSGPRYYAFDLIA--QRVTRV--ARGNKWLNCRYGx-----------------------
p08253.swisspro    FFKGAYYLKLENQS-LKSV-KFG-SIKSDWLGCx--------------------------
hs4cola.pep        FCQDRFYWRVSSRSELNQVDQVG-YVTYDILQCPEDx-----------------------
hsmmp3a.pep        FFTGSSQLEFDPNA--KKVTHT--LKSNSWLNCx--------------------------
hsstrom2.pep       FFSGSSQFEFDPNA--RMVTHI--LKSNSWLHCx--------------------------
hsstrol3.pep       FLRGRLYWKFDP-VKVKALEGFPRLVGPDFFGCAEPANTFLx------------------
                                                    *
                                 +                  +

MMPmla.pep         EVIIIEVDEEGGG------------------------AVSAAAVVLPVTLLLLVLAVGLAVF
MMPmlb.pep         EVIIIEVDEEGGG------------------------AVSAAAVVLPVTLLLLVLAVGLAVF
MMPm2.pep          DSAEGDVGDGDGDFGAGVNKDGGSRVVVQMEEVARTVNVMVLVPLLLLCVLGLTYALV
hscollr.pep        ------------------------------------------------------------
hsclgna.pep        ------------------------------------------------------------
p08253.swisspro    ------------------------------------------------------------
hs4cola.pep        ------------------------------------------------------------
hsmmp3a.pep        ------------------------------------------------------------
hsstrom2.pep       ------------------------------------------------------------
hsstrol3.pep       ------------------------------------------------------------
```

FIG. 3H

```
MMPm1a.pep         FFRRHGTPRRLLYCQRSLLDKVx
MMPm1b.pep         FFRRHGTPRRLLYCQRSLLDKVx
MMPm2.pep          QMQRKGAPRVLLYCKRSLQEWVx
hscollr.pep        -----------------------
hsclgna.pep        -----------------------
p08253.swisspro    -----------------------
hs4cola.pep        -----------------------
hsmmp3a.pep        -----------------------
hsstrom2.pep       -----------------------
hsstrol3.pep       -----------------------
```

DNA SEQUENCES FOR MATRIX METALLOPROTEASES, THEIR PRODUCTION AND USE

This application is a continuation of Ser. No. 08/704,711 filed Nov. 20, 1996, now U.S. Pat. No. 6,114,159 which is a 371 of PCT/DE95/00357 filed Mar. 17, 1995.

BACKGROUND OF THE INVENTION

The invention relates to DNA sequences for human matrix metalloproteases as well as to homologous sequences derived therefrom. It furthermore relates to the proteins and protein variants, coded by the DNA sequences, their expression, preparation and utilization. Areas of application are molecular biological, medical and pharmaceutical research, medical diagnosis and therapy and the pharmaceutical and biotechnological industry.

Matrix metalloproteases hydrolyze proteins of the extra-cellular matrix. They change the matrix structure and effect cell-matrix interactions. The matrix metalloproteases include collagenases, gelatinases, stromelysins and metalloelastases [1]. The following are some of the physiological processes, in which the enzymes participate: ovulation [2], embryo implantation in the uterus [3], cell migrations and tissue inversions during embryo genesis [4], involution of the mammary gland [5] and of the uterus [6] and angiogenesis [7]. Matrix metalloproteases play an important role in wound healing and scar formation [8], in metastasizing of tumors cells [9, 10], in rheumatic arthritis and osteoarthritis [11, 12] and in periodontal diseases [13].

All matrix metalloproteases contain a $Zn^{2+}$ ion in the active center. The activation of the matrix metalloproteases, synthesized in the form of inactive pro-enzymes, requires the dissolution of a bond between the $Zn^{2+}$ ion in the active center and a Cys group in the it-terminal propeptide of matrix metalloproteases (cysteine switch) [14]. Matrix metalloproteases consist of several protein domains, which exhibit homology among members of the Protease family [1, 14]. Whereas the protease matrilysin consists only of a propeptide and of the amino acid sequence of the catalytic domain, other matrix metalloproteases contain, in addition, a hemopexin-like sequence of about 200 amino acids. The gelatinases A and B contain additional amino acid sequences. Known human matrix metalloproteases, their molecular weights and their preferred substrates are listed in Table 1.

TABLE 1

MATRIX METALLOPROTEASES

| Protease | $M_r$ (kDa) | Substrate |
| --- | --- | --- |
| Interstitial Collagenase (MMP-1) | 54.1 | Collagen I, II, III |
| Neutrophilic Collagenase (MMP-5) | 53.4 | Collagen I, II, III |
| Gelatinase A (MMP-2) | 73.9 | Collagen IV, V, VII Gelatin, Elastin |
| Gelatinase B (MMP-9) | 78.4 | Collagen IV, V Gelatin, Elastin |
| Stromelysin 1 (MMP-3) | 54 | Proteoglycans, Fibronectin, Laminin, Gelatin, Collagen II, IV, V, IX |
| Stromelysin 2 (MMP-10) | 54.1 | Proteoglycans, Fibronectin, Laminin, Gelatin, Collagen II, IV, V, IX |
| Matrilysin (MMP-7) | 29.7 | Proteoglycans, Fibronectin, Gelatin, Elastin |
| Stromelysin 3 | 54.6 | |
| Metalloelastase | 54 | Fibronectin, Elastin |

The different matrix metalloproteases are distinguished not only by a characteristic, macromolecular specificity for matrix proteins. Their activity is controlled on different molecular and cellular levels:

1. Regulation of the synthesis of matrix metalloproteases by growth factors, cytokines, polypeptide hormones, prostaglandins, glucocorticoids, estrogen, progesterone and other effectors [1, 14].
2. Binding of matrix metalloproteases to membrane a receptors [15].
3. Activation of inactive proenzymes by specific hydrolysis of the respective propeptides [16] or by oxidation [17].
4. Inhibition of matrix metalloproteases by specific protein inhibitors such as TIMP-1, TIMP-2 and TIMP-3 (TIMP=Tissue Inhibitor of Matrix Metalloproteases) [16].
5. Proteolytic degradation of matrix metalloproteases.

Matrix metalloproteases are being investigated intensively because of their important physiological functions and their role in the pathogenesis of diseases. There is interest in finding and characterizing further matrix metalloproteases.

SUMMARY OF THE INVENTION

It is an object of the present invention to make accessible novel and previously unknown human matrix metalloproteases for medical research, diagnosis and therapy. The task consists of identifying and isolating DNA sequences for matrix metalloproteases and of characterizing the proteins coded by the DNA sequences.

Novel matrix metalloproteases are discovered by the following method. In sequences of known matrix metalloproteases, conserved amino acid sequences are selected. Two suitable sequences are amino acids about a conserved Cys group in the propeptide (cysteine switch) and amino acids, which participate in the $Zn^{2+}$ binding in the active center of the enzymes. Oligonucleotides are synthesized for the selected peptides. Polymerase chain reactions (PCR) are carried out with the oligonucleotides and cDNA, which can be obtained by reverse transcription of mRNA from cells and tissue. Synthesized DNA fragments are cloned and sequenced. The sequences determined are compared with sequences in gene data banks. PCR products with novel, previously unknown nucleotide sequences and homologous with DNA sequences of matrix metalloproteases are used as probes for determining the gene expression and for obtaining complete cDNA sequences from cDNA libraries. The nucleotide sequences of complete cDNA are determined. The amino acid sequences of the corresponding proteins are derived by translation of the coding nucleotide regions and analyzed by known methods.

BRIEF DESCRIPTION OF THE DRAWINGS

FIGS. 2A and 2B show the Northern Blot Analysis of mRNA for MMPm1 (FIG. 2A) and MMPm2 (FIG. 2B) in different human tissue.

FIGS. 3A–H show the homology comparison of MMPm1a (SEQ ID NO: 1), MMPm1b (SEQ ID NO:2) and MMPm2 (SEQ ID NO:3) with known human matrix metalloproteases. The comparison was carried out with the CLUSTAL program. Key for the abbreviations in the figures: hscollr.pep (SEQ ID NO:16)—interstitial collagenase, hsclgna.pep (SEQ ID NO: 17)—netrophile collagenases, PO8253, swisspro (SEQ ID NO:18)—gelatinase A, hs4cola.pep (SEQ ID NO:19)—gelatinase B, hsmmp3a.pep (SEQ ID NO:20)—stromelysin 1, hsstrom2.pep (SEQ ID NO:21)—stromelysin 2, hsstrol3.pep (SEQ ID NO:22)—stromelysin 3.

DETAILED DESCRIPTION OF THE INVENTION

Figure 1:
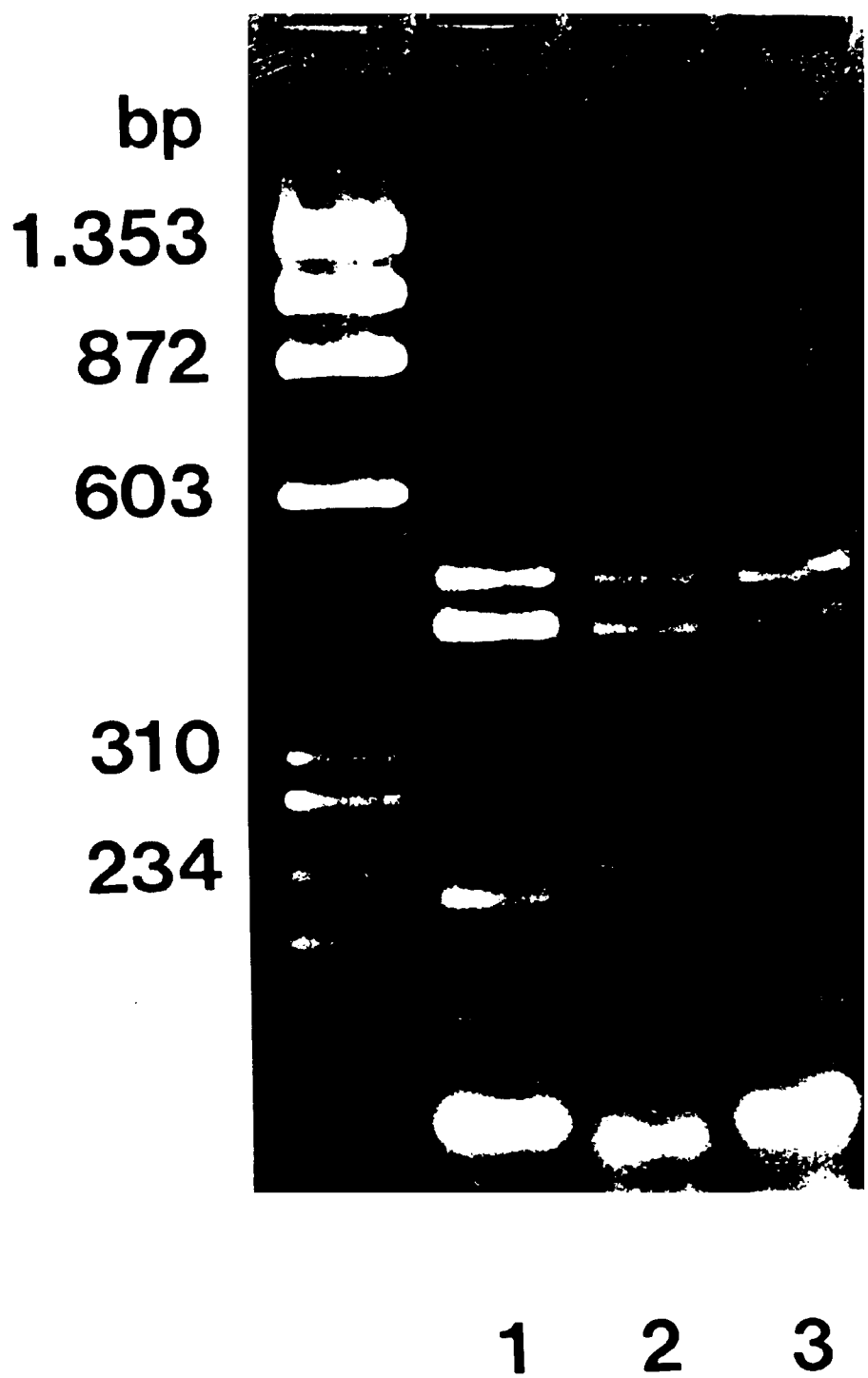
FIG. 1 shows an agarose gel electrophoresis of PCR products, which were obtained with degenerated primers for matrix metalloproteases and cDNA of the human neuroblastoma cell line SK-N-SH (lane 1), cDNA of kidney carcinoma tissue (lane 2) and cDNA of osteosarcoma tissue (lane 3).

The following cDNA sequences are found:
1. A cDNA sequence mmpm1a (Seq. ID No.:8) consisting of
   a 5' nontranslated region: base pairs 1 to 141
   a coding region: base pairs 142 to 1881
   a 3' nontranslated region: base pairs 1882 to 3456
2. A cDNA sequence mmpm1b (Seq. ID No.:9) consisting of
   a 5' nontranslated region: base pairs 1 to 113
   a coding region: base pairs 114 to 1862
   a 3' nontranslated region: base pairs 1863 to 3437
3. A cDNA sequence mmpm2 (Seq. ID No.:10) consisting of
   a 5' nontranslated region: base pairs 1 to 48
   a coding region: base pairs 49 to 2058
   a 3' nontranslated region: base pairs 2059 to 3530

The invention also comprises variants of these sequences as well as homologous DNA sequences of man and other mammalian species, which are found by cross-hybridization with these sequences. The invention also comprises constructs, which consist of a vector for the gene transfer in prokaryotic or eukaryotic cells and one of the inventive sequences.

Different aspects of the biosynthesis of coded matrix metalloproteases can be investigated with the help of the sequences mmpm1a, mmpm1b and mmpm2. The structure of the genes, including flanking sequences, can be determined. cDNA sequences can be used as molecular probes for analyzing the gene expression in cells and tissue.

The cDNA sequences mmpm1a (SEQ ID NO:8), mmpm1b (SEQ ID NO:9) and mmpm2 (SEQ ID NO:10) code encode the protein with the following amino acid sequences MMPm1a (SEQ ID NO:1), MMPm1b (SEQ ID NO;2) and MMPm2 (SEQ ID NO:3), respectively.

The invention also comprises variants of these proteins, which are obtained by post-translational protein modifications, by chemical modifications of the proteins or by in vitro mutagenesis and expression of nucleotide sequences, as well as of homologous proteins of man and other mammalian species, which are identified by immunological cross-reactivity or comparable enzyme activity. The invention also comprises complexes of these proteins with one or several ligands.

MMPm1a (SEQ ID NO:1), MMPm1b (SEQ ID NO:2) and MMPm2 (SEQ ID NO:3) can also be isolated from natural sources. The proteins can also be synthesized by gene transfer and expression in prokaryotic and eukaryotic cells and obtained from the recombinant cells. The availability of the proteins MMPm1a, MMPm1b and MMPm2 enables their structure and function to be investigated. Methods for determining enzymatic activity and specificity can be worked out. beginning with the primary structure of the proteins MMPm1a, MMPm1b and MMPm2, monoclonal and polycolonal antibodies can be produced. The antibodies can be used for the diagnostic analysis of MMPm1a, MMPm1b and MMPm2. MMPm1a, MMPm1b and MMPm2 can be used as test structures for finding natural and synthetic activators and inhibitors of matrix metalloproteases.

The following additional statements can be made concerning the characterization of mmpm1a, mmpm1b and mmpm2 and of MMPm1a, MMPm1b and MMPm2. The DNA sequences mmpm1a and mmpm1b differ only in their 5' nontranslated regions and in the immediately subsequent parts of their coding regions. starting with the nucleotides 363 (mmpm1a) and 344 (mmpm1b) respectively, the two sequences are identical. The mmpm1a sequence contains an open reading frame of 580 codons. The reading frame commences with the nucleotides $A_{142}TG$. However, the surroundings of these nucleotides are unfavorable for a effective translation. On the other hand, the subsequent nucleotides $A_{154}TG$ in the reading frame are in an environment favoring a translation start. It is possible that the translation of mmpm1a commences only at the $A_{154}TG$. Starting with $A_{114}TG$, the mmp1b sequence has an open reading frame of 583 codons. The starting codon is within the nucleotide sequence ACCATGT, which favors an effective translation. The translation start of mmpm2 is found at $A_{49}TG$. The open reading frame of mmpm2 contains 670 codons.

The proteins MMPm1a, MMPm1b and MMPm2, which are encoded by the cDNA sequences mmpm1a, mmpm1b and mmpm2, have calculated molecular weights of 65,591, 65,900 and 75,813. The primary sequences of MMPm1a, MMPm1b and MMPm2 are homologous with sequences of known matrix metalloproteases. Each of the three novel enzymes contains a signal peptide, a prosequence with the cysteine switch region PRCGVPD (Seq. ID No.:11) and a consensus sequence RRKRYA (Seq. ID No.:12). Catalytic domains with the specific arrangement of three histidine groups HELGHALGLEH (Seq. ID No.:13) and sequences homologous with hemopexin follow. In contrast to known matrix metalloproteases, MMPm1a, MMPm1b and MMPm2 furthermore contain C-terminal sequences with characteristic sequences of hydrophobic amino acid groups. MMPm1a and MMPm1b have the hydrophobic amino acid sequence AAAVVLLLLLVLAVGLAV (amino acid positions 536–556 in MMPm1a, amino acid positions 539–559 in MMPm1b). An analogous sequence in MMPm2 is VVMVLVPLLLLLCVLGLTY (amino acid groups 626–645). The hydrophobic sequences, which go beyond the positions given, are flanked by charged amino acid groups. N-terminally, negatively charged glutamine and aspartate groups predominate and C-terminally, positively charged arginine and lysine groups predominate.

The presence of the hydrophobic sequences in MMPm1a, MMPm1b and MMPm2 permits the conclusion to be drawn that MMPm1a, MMPm1b and MMPm2, contrary to known soluble matrix metalloproteases (Table 1), are membrane-associated enzymes. It follows from the primary sequences that propeptides, catalytic domains and domains of the proteases, homologous with hemopexin, are localized extracellularly. The outermost C terminal of the proteins, on the other hand, should be located in the cytosol of cells expressing MMPm1a, MMPm1b and MMPm2.

MMPm1a, MMPm1b and MMPm2 contain a potential glycosylating site at.

MMPm1a and MMPm1b differ only in their signal and prosequences. The different structure of the prosequences implies different activation mechanisms of MMPm1a and MMPm1b. Since the prosequences are cleaved off by hydrolysis in the course of the activation of matrix metalloproteases, the activation of MMPm1a and MMPm1b should lead to an identical, active enzyme.

As shown in FIG. 2A and 2B, Northern blot analyses of mRNA of human tissue confirm that MMPm1 and MMPm2 are expressed differently. Matrix metalloproteases of the MMPm1 type are expressed primarily in lung, placenta, kidney, ovary, prostate, small intestine, spleen, thymus and testicle tissue. Their expression is clearly less in heart and pancreas tissue and hardly detectable in the brain, liver and skeletal muscles. MMPm2 is expressed in the placenta, heart, liver, skeletal muscles, kidneys, pancreas, lung, testicle, colon and small intestine.

In summary, it is noted that the invention makes available novel, previously not known matrix metalloproteases of man. A knowledge of the cDNA and protein sequences of the matrix metalloproteases permits the biosynthesis, structure and function of the enzymes to be investigated further. Inherited and acquired mutations can be found by analyzing gene sequences. Diagnostic information can be obtained from determining the concentration and activity of matrix metalloproteases in cells, tissues and exoreta. The enzymes can be used advantageously as test structures for discovering new pharmaceutical drugs, including activators and inhibitors of matrix metalloproteases.

The invention is described further by the following examples:

1. Identification of Novel DNA Sequences for Matrix Metalloproteases

For finding cDNA sequences, which code for matrix metalloproteases, mRNA was isolated from human cell and tumor tissue, including neuroblastoma cells, kidney carcinoma and osteosarcoma tissue. The mRNA was transcribed into cDNA with reverse transcriptase.

Two preserved amino acid sequences were selected from the protein sequences of known matrix metalloproteases.

1. A sequence about a characteristic Cys group in propeptides in matrix metalloproteases P-R-C-G-V/N-P-D (Seq. ID No.:4)

2. A sequence with three His groups in the catalytic protein domain of matrix metalloproteases ($Zn^{2+}$ binding region):

H-E-L/I/F-G-H-S/V/A-L/M-G (Seq. ID No.:5)

Corresponding to the amino acid sequences, degenerate oligo-nucleotide primers, which take into consideration the variation of the amino acids in the two conserved sequences, as well as the degeneracy of the genetic code, were synthesized:

1. Propeptide primer (Seq. ID No.:6)

```
5'- NN TCT AGA CCC AGI TGT GGI GTI CCI GA -3'
              C      AA
```

2. Zn binding: region primer (Seq. ID No.:7)

```
5'- NN GGA TCC CC CAT IGA ATG ICC IAI TTC ATG -3'
               G CC  G           C   G
```

Both primers contain four desoxyinosine nucleotides as well as additional nucleotides for identification sites of the restriction endonucleases XbaI (propeptide primer) and BamHI ($zn^{2+}$ binding region primer).

The degenerated primers were used together with cDNA in the PCR.

The reaction mixture contained:

100 ng cDNA

1 μg propeptide primer

1 μg $Zn^2$ bonding region primer 2.5U/100 μL DNA polymerase AmpliTaq

100 μM dNTP 0.01% gelatin 50 mM KCl 1.5 mM $MgCl_2$ 10 mM Tris HCl, pH 8.3

In all, 30 reaction cycles of the sequence, 50 seconds at 94° C., 1 minute at 56° C. and 2 minutes at 72° C., were carried out. The amplified DNA was extracted with phenol/chloroform and subsequently treated with the restriction enzymes XbaI and BamHI. DNA fragments, ranging in size from 350 to 500 base pairs, were isolated by Agarose gel electrophoresis (FIG. 1) and cloned in the plasmid pBluescript SK (Stratagene). Individual clones were sequenced with T3 and T7 primers and sequence 2.0 (USB/Amersham Life Science). The sequences obtained were compared with DNA sequences in the Genbank and EMBL data banks. The sequences were compared with the FASTA program of the HUSAR (GCG Package, Copyright Genetics Computer Group, Inc.) program package. Beginning with the kidney carcinoma cDNA, for example, several hundred clones with amplified DNA were obtained, of which 50 were sequenced. The evaluation revealed known as well as novel DNA sequences. The former included sequences for human interstitial collagenase and for matrilysin. The latter included two sequences homologous to human matrix metalloproteases. The two novel sequences, which were named PCRmmpm1 and PCRmmpm2, contain the nucleotides, of SEQ ID NO:14 and SEQ ID NO:15, respectively.

2. Northern Blot Analysis

The expression of matrix metalloproteases in human tissue was investigated with the help of the PCRmmpm1 and PCRmmpm2 fragments. The fragments were labeled radioactively (Multiprime DNA-Labeling Kit, Amersham Life Science) and hybridized with mRNA on nylon (Multiple Tissue Blot, Clontech). The hybridizations and subsequent washings took place under standard conditions [18].

PCRmmpm1 and PCRmmpm2 hybridized with RNA of about 3.6 kb. However, experiments confirm a different 43 expression of the mRNA hybridizing with PCRmmpm1 and PCRmmpm2 (FIGS. 2A and 2B). Specific transcripts, which hybridize with PCRmmpm1, are contained particularly in lung, placenta, kidney and kidney carcinoma tissue (not shown). They are represented in clearly lesser amounts in pancreas and heart tissue and hardly at all in the liver, skeletal muscle and brain.

Messenger RNA, which hybridizes with PCRmmpm2, is synthesized particularly in placenta tissue. Its expression, however, is comparable in the heart, liver, skeletal muscle, kidneys, pancreas and lung and clearly less in brain tissue.

3. Isolation and sequencing of cDNA mmpm1 and mmpm2

A lung cDNA bank in the λgt 11 vector (Clontech) was analyzed by means of phage transfer on nylon and hybridization with the radioactively labeled PCRmmpm1 and PCRmmpm2 probes [18]. The hybridizations were carried out for 16 hours at 40° C. in 50% formamide, 5×SSPE, 5×Denhardt, 0.5% SDS and 50 µg/ml denatured herring sperm DNA. After the hybridization, the filters were washed at room temperature and at 65° C. in 2×SSC, 0.1% SDS and subsequently evaluated in a Bio-Imaging-Analyzer (BAS 2000, Fuji Photo Film Co., LTD). Phage clones, which hybridized with PCRmmpm1 and PCRmmpm2, were identified by means of specifically bound radioactivity. The phages found were isolated stepwise by dilution. The DNA of isolated phages was isolated (Quiagen Lambda Kit, Diagen GmbH) and the cDNA inserts contained were inserted into the plasmid vector pbluescript SK (Stratagene). The inserts subsequently were divided into partial fragments (Erase-a-Base-System, Promega) and sequenced (Sequence 2.0, USB/Amersham Life Science). DNA sequences detected were analyzed with the help of the DNA-STAR (DAN-STAR. Inc) and HUSAR (GCT Package, Copyright Genetics Computer Group, Inc) program packages. The translation of the coding sequences and the comparison of the amino acid sequences obtained with known matrix metalloproteases confirmed-that the novel sequences belong to the family of matrix metalloproteases (FIGS. 3A–3D).

REFERENCES

1. Matrisian, L. M. (1992) Bioassays 14, 455–463
2. curry, T. E. jr, Mann, J. S., Estes, R. J. and Jones, P. B. C. (1990) Endocrinology 127, 63–68
3. Librach, C. L., Werb, Z., Fitzgerald, M. L., Chiu, K., Corwin, N. M., Esteves, R. A., Grobelny, D., Galardy, R., Damsky, C. H. and Fisher, S. J. (1991) J. Cell Biol. 113, 437–449
4. Brenner, C. A., Adler, R. R., Rappolee, D. A., Pedersen, R. A. and Werb, Z. (1989) Genes Development 3, 848–859
5. Talhouk, R. S., Bissel, M. J. and Werb, Z. (1992) J. Cell Biol. 118, 1271–1282
6. Woessner, J. F and Taplin, C. (1988) J. Biol. Chem. 263, 16918–16925
7. Folkman, J. and Shing, Y. (1992) J. Biol. Chem. 267, 10931–10934
8. Sakamoto, S. and Sakamoto, M. (1988) Mol. Aspects Med. 10, 301–428
9. Mignatti, P. and Rifkin, D. B. (1993) Physiol. Rev. 73, 161–195
10. Stetler-Stevenson, W. G., Liotta, L. A. and Kleiner, D. E. jr (1993), FASEB J. 7, 1434–1441
11. Dean, D. D., Martel-Pelletier, J., Pelletier, J.-P., Howell, D. S. and Woessner, J. F. jr, (1989) J. Clin. Invest. 84, 678–685
12. McCachren, S. S. (1991) Arthritis Rheum. 34, 1085–1093
13. Birkedahl-Hansen, H. (1993) J. Periodontol. 64, 474–484
14. Woessner, J. F. jr (1991) FASEB J. 5, 2145–2154
15. Monsky, W. L., Kelly, T., Lin, C.-Y., Yeh, Y., Stetler-Stevenson, W. G., Mueller, S. C. and Chen, W.-T. (1993) Cancer Res. 53, 3159–3164
16. Kleiner, D. E. jr and Stetler-Stevenson, W. G. (1993) Curr. Opinion Cell Biol. A, 891–897
17. Weiss, S. J., Peppin, G., Ortiz, X., Ragsdale, C. and Test, S. T. (1985) Science 227, 747–749
18. Sambrook, J., Fritsch, D. F. and Maniatis, T. (1989) Molecular Cloning. A Laboratory Manual. 2nd Edition. Cold Spring Harbor Laboratory Press.

---

What is claimed is:

1. An isolated DNA sequence encoding a matrix metalloprotease, wherein said DNA sequence comprises
    a DNA sequence encoding SEQ ID NO: 1; or
    a DNA sequence that hybridizes to SEQ ID NO: 8 at 40° C. in a solution of 50% formamide in 5×SSPE/5× Denhardt solution containing 0.5 SDS and 50 μg/ml denatured carrier DNA, followed by a wash at 65° in 2×SSC, 0.1% SDS.

2. The isolated DNA sequence of claim 1, wherein said DNA sequence is a DNA sequence encoding SEQ ID NO:1.

3. A prokaryotic or eukaryotic vector comprising a DNA sequence of claim 1.

4. The vector of claim 3 comprising the DNA sequence encoding SEQ ID NO:1.

5. A prokaryotic or eukaryotic cell transformed with the vector of claim 3, wherein said cell expresses a matrix metalloprotease encoded by said DNA sequence.

6. The cell of claim 5, wherein said DNA sequence is a DNA sequence encoding SEQ ID NO:1.

7. A method of producing a matrix metalloprotease comprising:
    i) culturing recombinant cells expressing a
        DNA sequence encoding a matrix metalloprotease selected from the group consisting of a DNA sequence encoding SEQ ID NO: 1; or
        a DNA sequence that hybridizes to SEQ ID NO: 8 at 40° C. in a solution of 50% formamide in 5×SSPE/ 5× Denhardt solution containing 0.5% SDS and 50 pg/ml denatured carrier DNA, followed by a wash at 65° in 2×SSC, 0.1% SDS; and
    ii) isolating the matrix metalloprotease.

8. An isolated DNA sequence encoding a matrix metalloprotease, wherein said DNA sequence comprises
    a DNA sequence encoding SEQ ID NO: 2 or
    a DNA sequence that hybridizes to SEQ ID NO: 9 at 40° C. in a solution of 50% formamide in 5×SSPE/5× Denhardt solution containing 0.5 SDS and 50 μg/ml denatured carrier DNA, followed by a wash at 65° in 2×SSC, 0.1% SDS.

9. A prokaryotic or eukaryotic vector comprising a DNA sequence of claim 8.

10. A prokaryotic or eukaryotic cell transformed with the vector of claim 9, wherein said cell expresses a matrix metalloprotease encoded by said DNA sequence.

11. The isolated DNA sequence of claim 8, wherein said DNA sequence is a DNA sequence encoding SEQ ID NO: 2.

12. A method of producing a matrix metalloprotease comprising:
    i) culturing recombinant cells expressing a DNA sequence encoding a matrix metalloprotease selected from the group consisting of a DNA sequence encoding SEQ ID NO: 2; or
        a DNA sequence that hybridizes to SEQ ID NO: 9 at 40° C. in a solution of 50% formamide in 5×SSPE/

5× Denhardt solution containing 0.5% SDS and 50 pg/ml a denatured carrier at 65° in 2×SSC, 0.1% SDS; and isolating the matrix metalloprotease.

13. An isolated DNA sequence encoding a matrix metalloprotease, wherein said DNA sequence comprises a DNA sequence encoding SEQ ID NO: 3 or a DNA sequence that hybridizes to SEQ ID NO: 10 at 40° C. in a solution of 50% formamide in 5×SSPB/5× Denhardt solution containing 0.5 SDS and 50 μg/ml denatured carrier DNA, followed by a wash at 65° in 2×SSC, 0.1% SDS.

14. The isolated DNA sequence of claim 11, wherein said DNA sequence is a DNA sequence encoding SEQ ID NO: 3.

15. A prokaryotic or eukaryotic vector comprising a DNA sequence of claim 13.

16. A prokaryotic or eukaryotic cell transformed with the vector of claim 15, wherein said cell expresses a matrix metalloprotease encoded by said DNA sequence.

17. A method of producing a matrix metalloprotease comprising:

i) culturing recombinant cells expressing
DNA sequence encoding a matrix metalloprotease selected from the group consisting of a DNA sequence encoding SEQ ID NO: 3; or a DNA sequence that hybridizes to SEQ ID NO: 10 at 40° C. in a solution of 50% formamide in 5×SSPE/ 5× Denhardt solution containing 0.5% SDS and 50 pg/ml denatured carrier DNA, followed by a wash at 65° in 2×SSC, 0.1% SDS; and ii) isolating this matrix metalloprotease.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 579 amino acids
      (B) TYPE: amino acid
      (C) STRANDEDNESS: single
      (D) TOPOLOGY: linear (xi) SEQUENCE DESCRIPTION: SEQ ID NO: 1:

```
Met Thr Tyr Glu Met Glu His Leu Phe Arg C ys Leu Phe Ala Ala Cys
 1               5                  10                  15

Val Ser Ser Leu Val Phe Gly Ser Phe Phe A sn His Val Val Ser Phe
                20                  25                  30

Ser Phe Leu Phe Phe Glu Ser Leu Ala Leu S er Ser Gly Val Glu Cys
                35                  40                  45
```

-continued

```
Asn Gly Ala Ile Ser Ala Tyr Cys Asn Leu Cys Leu Leu Gly Ser Ser
 50                  55                  60

Asp Ser Pro Ala Ser Ala Ser Gln Ile Ala Gly Lys Ala Asp Ala Asp
 65                  70                  75                  80

Thr Met Lys Ala Met Arg Arg Pro Arg Cys Gly Val Pro Asp Lys Phe
                 85                  90                  95

Gly Ala Glu Ile Lys Ala Asn Val Arg Arg Lys Arg Tyr Ala Ile Gln
            100                 105                 110

Gly Leu Lys Trp Gln His Asn Glu Ile Thr Phe Cys Ile Gln Asn Tyr
             115                 120                 125

Thr Pro Lys Val Gly Glu Tyr Ala Thr Tyr Glu Ala Ile Arg Lys Ala
             130                 135                 140

Phe Arg Val Trp Glu Ser Ala Thr Pro Leu Arg Phe Arg Glu Val Pro
145                 150                 155                 160

Tyr Ala Tyr Ile Arg Glu Gly His Glu Lys Gln Ala Asp Ile Met Ile
                165                 170                 175

Phe Phe Ala Glu Gly Phe His Gly Asp Ser Thr Pro Phe Asp Gly Glu
            180                 185                 190

Gly Gly Phe Leu Ala His Ala Tyr Phe Pro Gly Pro Asn Ile Gly Gly
             195                 200                 205

Asp Thr His Phe Asp Ser Ala Glu Pro Trp Thr Val Arg Asn Glu Asp
             210                 215                 220

Leu Asn Gly Asn Asp Ile Phe Leu Val Ala Val His Glu Leu Gly His
225                 230                 235                 240

Ala Leu Gly Leu Glu His Ser Ser Asp Pro Ser Ala Ile Met Ala Pro
                245                 250                 255

Phe Tyr Gln Trp Met Asp Thr Glu Asn Phe Val Leu Pro Asp Asp Asp
            260                 265                 270

Arg Arg Gly Ile Gln Gln Leu Tyr Gly Glu Ser Gly Phe Pro Thr
             275                 280                 285

Lys Met Pro Pro Gln Pro Arg Thr Thr Ser Arg Pro Ser Val Pro Asp
290                 295                 300

Lys Pro Lys Asn Pro Thr Tyr Gly Pro Asn Ile Cys Asp Gly Asn Phe
305                 310                 315                 320

Asp Thr Val Ala Met Leu Arg Gly Glu Met Phe Val Phe Lys Glu Arg
                325                 330                 335

Trp Phe Trp Arg Val Arg Asn Asn Gln Val Met Asp Gly Tyr Pro Met
             340                 345                 350

Pro Ile Gly Gln Phe Trp Arg Gly Leu Pro Ala Ser Ile Asn Thr Ala
             355                 360                 365

Tyr Glu Arg Lys Asp Gly Lys Phe Val Phe Phe Lys Gly Asp Lys His
             370                 375                 380

Trp Val Phe Asp Glu Ala Ser Leu Glu Pro Gly Tyr Pro Lys His Ile
385                 390                 395                 400

Lys Glu Leu Gly Arg Gly Leu Pro Thr Asp Lys Ile Asp Ala Ala Leu
                405                 410                 415

Phe Trp Met Pro Asn Gly Lys Thr Tyr Phe Phe Arg Gly Asn Lys Tyr
            420                 425                 430

Tyr Arg Phe Asn Glu Glu Leu Arg Ala Val Asp Ser Glu Tyr Pro Lys
             435                 440                 445

Asn Ile Lys Val Trp Glu Gly Ile Pro Glu Ser Pro Arg Gly Ser Phe
450                 455                 460
```

```
Met Gly Ser Asp Glu Val Phe Thr Tyr Phe Tyr Lys Gly Asn Lys Tyr
465                 470                 475                 480

Trp Lys Phe Asn Asn Gln Lys Leu Lys Val Glu Pro Gly Tyr Pro Lys
                485                 490                 495

Ser Ala Leu Arg Asp Trp Met Gly Cys Pro Ser Gly Gly Arg Pro Asp
                500                 505                 510

Glu Gly Thr Glu Glu Thr Glu Val Ile Ile Ile Glu Val Asp Glu
                515                 520                 525

Glu Gly Gly Gly Ala Val Ser Ala Ala Val Val Leu Pro Val Leu
                530                 535                 540

Leu Leu Leu Leu Val Leu Ala Val Gly Leu Ala Val Phe Phe Arg
545                 550                 555                 560

Arg His Gly Thr Pro Arg Arg Leu Leu Tyr Cys Gln Arg Ser Leu Leu
                565                 570                 575

Asp Lys Val (2) INFORMATION FOR SEQ ID NO: 2:

(i) SEQUENCE CHARACTERISTICS:
        (A) LENGTH: 582 amino acids
        (B) TYPE: amino acid
        (C) STRANDEDNESS: single
        (D) TOPOLOGY: linear (xi) SEQUENCE DESCRIPTION: SEQ ID NO: 2:

Met Ser Pro Ala Pro Arg Pro Pro Arg Cys Leu Leu Leu Pro Leu Leu
1               5                   10                  15

Thr Leu Gly Thr Ala Leu Ala Ser Leu Gly Ser Ala Gln Ser Ser Ser
                20                  25                  30

Phe Ser Pro Glu Ala Trp Leu Gln Gln Tyr Gly Tyr Leu Pro Pro Gly
                35                  40                  45

Asp Leu Arg Thr His Thr Gln Arg Ser Pro Gln Ser Leu Ser Ala Ala
                50                  55                  60

Ile Ala Ala Met Gln Lys Phe Tyr Gly Leu Gln Val Thr Gly Lys Ala
65              70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
                100                 105                 110

Ala Ile Gln Gly Leu Lys Trp Gln His Asn Glu Ile Thr Phe Cys Ile
                115                 120                 125

Gln Asn Tyr Thr Pro Lys Val Gly Glu Tyr Ala Thr Tyr Glu Ala Ile
130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
                180                 185                 190

Asp Gly Glu Gly Gly Phe Leu Ala His Ala Tyr Phe Pro Gly Pro Asn
                195                 200                 205

Ile Gly Gly Asp Thr His Phe Asp Ser Ala Glu Pro Trp Thr Val Arg
                210                 215                 220

Asn Glu Asp Leu Asn Gly Asn Asp Ile Phe Leu Val Ala Val His Glu
225                 230                 235                 240
```

-continued

```
Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
                260                 265                 270

Asp Asp Asp Arg Arg Gly Ile Gln Gln Leu Tyr Gly Gly Glu Ser Gly
            275                 280                 285

Phe Pro Thr Lys Met Pro Pro Gln Pro Arg Thr Thr Ser Arg Pro Ser
        290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
                340                 345                 350

Tyr Pro Met Pro Ile Gly Gln Phe Trp Arg Gly Leu Pro Ala Ser Ile
                355                 360                 365

Asn Thr Ala Tyr Glu Arg Lys Asp Gly Lys Phe Val Phe Lys Gly
                370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
                420                 425                 430

Asn Lys Tyr Tyr Arg Phe Asn Glu Glu Leu Arg Ala Val Asp Ser Glu
                435                 440                 445

Tyr Pro Lys Asn Ile Lys Val Trp Glu Gly Ile Pro Glu Ser Pro Arg
        450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
        500                 505                 510

Arg Pro Asp Glu Gly Thr Glu Glu Glu Thr Glu Val Ile Ile Ile Glu
        515                 520                 525

Val Asp Glu Glu Gly Gly Gly Ala Val Ser Ala Ala Ala Val Val Leu
530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
                580
```

(2) INFORMATION FOR SEQ ID NO: 3:

(i) SEQUENCE CHARACTERISTICS:
        (A) LENGTH: 669 amino acids
        (B) TYPE: amino acid
        (C) STRANDEDNESS: single
        (D) TOPOLOGY: linear (xi) SEQUENCE DESCRIPTION: SEQ ID NO: 3:

```
Met Gly Ser Asp Pro Ser Ala Pro Gly Arg Pro Gly Trp Thr Gly Ser
1               5                   10                  15
```

-continued

```
Leu Leu Gly Asp Arg Glu Glu Ala Ala Arg Pro Arg Leu Leu Pro Leu
            20                  25                  30

Leu Leu Val Leu Leu Gly Cys Leu Gly Leu Gly Val Ala Ala Glu Asp
            35                  40                  45

Ala Glu Val His Ala Glu Asn Trp Leu Arg Leu Tyr Gly Tyr Leu Pro
 50                  55                  60

Gln Pro Ser Arg His Met Ser Thr Met Arg Ser Ala Gln Ile Leu Ala
 65                  70                  75                  80

Ser Ala Leu Ala Glu Met Gln Arg Phe Tyr Gly Ile Pro Val Thr Gly
            85                  90                  95

Val Leu Asp Glu Glu Thr Lys Glu Trp Met Lys Arg Pro Arg Cys Gly
           100                 105                 110

Val Pro Asp Gln Phe Gly Val Arg Val Lys Ala Asn Leu Arg Arg Arg
           115                 120                 125

Arg Lys Arg Tyr Ala Leu Thr Gly Arg Lys Trp Asn Asn His His Leu
           130                 135                 140

Thr Phe Ser Ile Gln Asn Tyr Thr Glu Lys Leu Gly Trp Tyr His Ser
145                 150                 155                 160

Met Glu Ala Val Arg Arg Ala Phe Arg Val Trp Glu Gln Ala Thr Pro
                165                 170                 175

Leu Val Phe Gln Glu Val Pro Tyr Glu Asp Ile Arg Leu Arg Arg Gln
                180                 185                 190

Lys Glu Ala Asp Ile Met Val Leu Phe Ala Ser Gly Phe His Gly Asp
                195                 200                 205

Ser Ser Pro Phe Asp Gly Thr Gly Phe Leu Ala His Ala Tyr Phe
210                 215                 220

Pro Gly Pro Gly Leu Gly Gly Asp Thr His Phe Asp Ala Asp Glu Pro
225                 230                 235                 240

Trp Thr Phe Ser Ser Thr Asp Leu His Gly Asn Asn Leu Phe Leu Val
                245                 250                 255

Ala Val His Glu Leu Gly His Ala Leu Gly Leu Glu His Ser Ser Asn
                260                 265                 270

Pro Asn Ala Ile Met Ala Pro Phe Tyr Gln Trp Lys Asp Val Asp Asn
                275                 280                 285

Phe Lys Leu Pro Glu Asp Asp Leu Arg Gly Ile Gln Gln Leu Tyr Gly
           290                 295                 300

Thr Pro Asp Gly Gln Pro Gln Pro Thr Gln Pro Leu Pro Thr Val Thr
305                 310                 315                 320

Pro Arg Arg Pro Gly Arg Pro Asp His Arg Pro Pro Arg Pro Pro Gln
                325                 330                 335

Pro Pro Pro Gly Gly Lys Pro Glu Arg Pro Pro Lys Pro Gly Pro
                340                 345                 350

Pro Val Gln Pro Arg Ala Thr Glu Arg Pro Asp Gln Tyr Gly Pro Asn
           355                 360                 365

Ile Cys Asp Gly Asp Phe Asp Thr Val Ala Met Leu Arg Gly Glu Met
           370                 375                 380

Phe Val Phe Lys Gly Arg Trp Phe Trp Arg Val Arg His Asn Arg Val
385                 390                 395                 400

Leu Asp Asn Tyr Pro Met Pro Ile Gly His Phe Trp Arg Gly Leu Pro
                405                 410                 415

Gly Asp Ile Ser Ala Ala Tyr Glu Arg Gln Asp Gly Arg Phe Val Phe
                420                 425                 430
```

```
Phe Lys Gly Asp Arg Tyr Trp Leu Phe Arg Glu Ala Asn Leu Glu Pro
            435                 440                 445

Gly Tyr Pro Gln Pro Leu Thr Ser Tyr Gly Leu Gly Ile Pro Tyr Asp
            450                 455                 460

Arg Ile Asp Thr Ala Ile Trp Trp Glu Pro Thr Gly His Thr Phe Phe
465                 470                 475                 480

Phe Gln Glu Asp Arg Tyr Trp Arg Phe Asn Glu Thr Gln Arg Gly
                485                 490                 495

Asp Pro Gly Tyr Pro Lys Pro Ile Ser Val Trp Gln Gly Ile Pro Ala
            500                 505                 510

Ser Pro Lys Gly Ala Phe Leu Ser Asn Asp Ala Ala Tyr Thr Tyr Phe
            515                 520                 525

Tyr Lys Gly Thr Lys Tyr Trp Lys Phe Asp Asn Glu Arg Leu Arg Met
            530                 535                 540

Glu Pro Gly Tyr Pro Lys Ser Ile Leu Arg Asp Phe Met Gly Cys Gln
545                 550                 555                 560

Glu His Val Glu Pro Gly Pro Arg Trp Pro Asp Val Ala Arg Pro Pro
                565                 570                 575

Phe Asn Pro His Gly Gly Ala Glu Pro Gly Ala Asp Ser Ala Glu Gly
            580                 585                 590

Asp Val Gly Asp Gly Asp Gly Asp Phe Gly Ala Gly Val Asn Lys Asp
            595                 600                 605

Gly Gly Ser Arg Val Val Val Gln Met Glu Glu Val Ala Arg Thr Val
            610                 615                 620

Asn Val Val Met Val Leu Val Pro Leu Leu Leu Leu Leu Cys Val Leu
625                 630                 635                 640

Gly Leu Thr Tyr Ala Leu Val Gln Met Gln Arg Lys Gly Ala Pro Arg
                645                 650                 655

Val Leu Leu Tyr Cys Lys Arg Ser Leu Gln Glu Trp Val
            660                 665

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 5
        (D) OTHER INFORMATION: /product= "OTHER"
            /note= "The Xaa at position 5 is Val or Asn."

(xi) SEQUENCE DESCRIPTION: SEQ ID NO: 4:

Pro Arg Cys Gly Xaa Pro Asp
1               5

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 3
        (D) OTHER INFORMATION: /product= "OTHER"
            /note= "The Xaa at position 3 is Leu, Ile or Phe."
```

```
    (ix) FEATURE:
         (A) NAME/KEY: Modified-site
         (B) LOCATION: 6
         (D) OTHER INFORMATION: /product= "OTHER"
              /note= "The Xaa at position 6 is Ser, Val or Ala ."

(ix) FEATURE:
         (A) NAME/KEY: Modified-site
         (B) LOCATION: 7
         (D) OTHER INFORMATION: /product= "OTHER"
              /note= "The Xaa at position 7 is Leu or Met."

(xi) SEQUENCE DESCRIPTION: SEQ ID NO: 5:

His Glu Xaa Gly His Xaa Xaa Gly
1               5

(2) INFORMATION FOR SEQ ID NO: 6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 6:

NNTCTAGACC CAGNTGYGGN RWNCCNGA                                      28

(2) INFORMATION FOR SEQ ID NO: 7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 7:

NNGGATCCCC CAKNSARTGN CCNANYTCRT G                                  31

(2) INFORMATION FOR SEQ ID NO: 8:

(i) SEQUENCE CHARACTERISTICS:
        (A) LENGTH: 3456 base pairs
        (B) TYPE: nucleic acid
        (C) STRANDEDNESS: single
        (D) TOPOLOGY: linear (xi) SEQUENCE DESCRIPTION: SEQ ID NO: 8:

ACCATTTTGC ATTCCCACAG CAGTGAATGA GAGCTCCTGT TTCTCCACAT T CTCACCAGC    60

ATTTGGTGTT GCTGGTGTTC TGGATTTTGG CCATTCTAAT AGGTGTGTCA T GGTATCTCA  120

TTGTTTTAAT TTGCATTTCT GATGACATAT GAGATGGAGC ATCTTTTCAG A TGCTTATTT  180

GCTGCCTGTG TATCTTCTTT GGTCTTTGGC TCATTTTTTA ATCACGTTGT T TCCTTTTCC  240

TTTCTTTTTT TTGAGAGTCT TGCTCTGTCA TCCGGGGTGG AGTGCAATGG T GCAATCTCA  300

GCCTACTGCA ACCTCTGTCT CCTGGGTTCA AGTGATTCTC CTGCCTCAGC C TCCCAAATA  360

GCTGGCAAAG CTGATGCAGA CACCATGAAG GCCATGAGGC GCCCCGATG T GGTGTTCCA   420

GACAAGTTTG GGCTGAGAT CAAGGCCAAT GTTCGAAGGA AGCGCTACGC C ATCCAGGGT   480

CTCAAATGGC AACATAATGA AATCACTTTC TGCATCCAGA ATTACACCCC C AAGGTGGGC   540

GAGTATGCCA CATACGAGGC CATTCGCAAG GCGTTCCGCG TGTGGGAGAG T GCCACACCA   600

CTGCGCTTCC GCGAGGTGCC CTATGCCTAC ATCCGTGAGG CCATGAGAA G CAGGCCGAC   660

ATCATGATCT TCTTTGCCGA GGGCTTCCAT GGCGACAGCA CGCCCTTCGA T GGTGAGGGC   720

GGCTTCCTGG CCCATGCCTA CTTCCCAGGC CCCAACATTG AGGAGACAC C CACTTTGAC   780
```

```
TCTGCCGAGC CTTGGACTGT CAGGAATGAG GATCTGAATG GAAATGACAT C TTCCTGGTG      840

GCTGTGCACG AGCTGGGCCA TGCCCTGGGG CTCGAGCATT CCAGTGACCC C TCGGCCATC      900

ATGGCACCCT TTTACCAGTG GATGGACACG GAGAATTTTG TGCTGCCCGA T GATGACCGC      960

CGGGGCATCC AGCAACTTTA TGGGGGTGAG TCAGGGTTCC CCACCAAGAT G CCCCCTCAA     1020

CCCAGGACTA CCTCCCGGCC TTCTGTTCCT GATAAACCCA AAAACCCCAC C TATGGGCCC     1080

AACATCTGTG ACGGGAACTT TGACACCGTG GCCATGCTCC GAGGGGAGAT G TTTGTCTTC     1140

AAGGAGCGCT GGTTCTGGCG GGTGAGGAAT AACCAAGTGA TGGATGGATA C CCAATGCCC     1200

ATTGGCCAGT TCTGGCGGGG CCTGCCTGCG TCCATCAACA CTGCCTACGA G AGGAAGGAT     1260

GGCAAATTCG TCTTCTTCAA AGGAGACAAG CATTGGGTGT TTGATGAGGC G TCCCTGGAA     1320

CCTGGCTACC CCAAGCACAT TAAGGAGCTG GGCCGAGGGC TGCCTACCGA C AAGATTGAT     1380

GCTGCTCTCT TCTGGATGCC CAATGGAAAG ACCTACTTCT TCCGTGGAAA C AAGTACTAC     1440

CGTTTCAACG AAGAGCTCAG GGCAGTGGAT AGCGAGTACC CCAAGAACAT C AAAGTCTGG     1500

GAAGGGATCC CTGAGTCTCC CAGAGGGTCA TTCATGGGCA GCGATGAAGT C TTCACTTAC     1560

TTCTACAAGG GGAACAAATA CTGGAAATTC AACAACCAGA AGCTGAAGGT A GAACCGGGC     1620

TACCCCAAGT CAGCCCTGAG GGACTGGATG GGCTGCCCAT CGGGAGGCCG G CCGGATGAG     1680

GGGACTGAGG AGGAGACGGA GGTGATCATC ATTGAGGTGG ACGAGGAGGG C GGCGGGGCG     1740

GTGAGCGCGG CTGCCGTGGT GCTGCCCGTG CTGCTGCTGC TCCTGGTGCT G GCGGTGGGC     1800

CTTGCAGTCT TCTTCTTCAG ACGCCATGGG ACCCCCAGGC GACTGCTCTA C TGCCAGCGT     1860

TCCCTGCTGG ACAAGGTCTG ACGCCCACCG CCGGCCCGCC CACTCCTACC A CAAGGACTT     1920

TGCCTCTGAA GGCCAGTGGC AGCAGGTGGT GGTGGGTGGG CTGCTCCCAT C GTCCCGAGC     1980

CCCCTCCCCG CAGCCTCCTT GCTTCTCTCT GTCCCCTGGC TGGCCTCCTT C ACCCTGACC     2040

GCCTCCCTCC CTCCTGCCCC GGCATTGCAT CTTCCCTAGA TAGGTCCCCT G AGGGCTGAG     2100

TGGGAGGGCG GCCCTTTCCA GCCTCTGCCC CTCAGGGGAA CCCTGTAGCT T TGTGTCTGT     2160

CCAGCCCCAT CTGAATGTGT TGGGGCTCT GCACTTGAAG GCAGGACCCT C AGACCTCGC     2220

TGGTAAAGGT CAAATGGGGT CATCTGCTCC TTTTCCATCC CCTGACATAC C TTAACCTCT     2280

GAACTCTGAC CTCAGGAGGC TCTGGGCACT CCAGCCCTGA AAGCCCCAGG T GTACCAAT     2340

TGGCAGCCTC TCACTACTCT TTCTGGCTAA AAGGAATCTA ATCTTGTTGA G GGTAGAGAC     2400

CCTGAGACAG TGTGAGGGGG TGGGACTGC CAAGCCACCC TAAGACCTTG G GAGGAAAAC     2460

TCAGAGAGGG TCTTCGTTGC TCAGTCAGTC AAGTTCCTCG GAGATCTGCC T CTGCCTCAC     2520

CTACCCCAGG GAACTTCCAA GGAAGGAGCC TGAGCCACTG GGACTAAGT G GGCAGAAGA     2580

AACCCTTGGC AGCCCTGTGC CTCTCGAATG TTAGCCTTGG ATGGGCTTT C ACAGTTAGA     2640

AGAGCTGAAA CCAGGGTGC AGCTGTCAGG TAGGGTGGGG CCGGTGGGAG A GGCCCGGGT     2700

CAGAGCCCTG GGGGTGAGCC TGAAGGCCAC AGAGAAAGAA CCTTGCCCAA A CTCAGGCAG     2760

CTGGGGCTGA GGCCCAAAGG CAGAACAGCC AGAGGGGGCA GGAGGGGACC A AAAAGGAAA     2820

ATGAGGACGT GCAGCAGCAT TGGAAGGCTG GGCCGGGCA GGCCAGGCCA A GCCAAGCAG     2880

GGGGCCACAG GGTGGGCTGT GGAGCTCTCA GGAAGGGCCC TGAGGAAGGC A CACTTGCTC     2940

CTGTTGGTCC CTGTCCTTGC TGCCCAGGCA GCGTGGAGGG GAAGGGTAGG G CAGCCAGAG     3000

AAAGGAGCAG AGAAGGCACA CAAACGAGGA ATGAGGGGCT TCACGAGAGG C CACAGGGCC     3060

TGGCTGGCCA CGCTGTCCCG GCCTGCTCAC CATCTCAGTG AGGGGCAGGA G CTGGGGCTC     3120

GCTTAGGCTG GGTCCACGCT TCCCTGGTGC CAGCACCCCT CAAGCCTGTC T CACCAGTGG     3180
```

```
CCTGCCCTCT CGCTCCCCCA CCCAGCCCAC CCATTGAAGT CTCCTTGGGC C ACCAAAGGT    3240

GGTGGCCATG GTACCGGGGA CTTGGGAGAG TGAGACCCAG TGGAGGGAGC A AGAGGAGAG    3300

GGATGTCGGG GGGGTGGGGC ACGGGGTAGG GGAAATGGGG TGAACGGTGC T GGCAGTTCG    3360

GCTAGATTTC TGTCTTGTTT GTTTTTTTGT TTTGTTTAAT GTATATTTTT A TTATAATTA    3420

TTATATATGA ATTCCAAAAA AAAAAAAAAA AAAAA                                3456
```

(2) INFORMATION FOR SEQ ID NO: 9:

(i) SEQUENCE CHARACTERISTICS:
        (A) LENGTH: 3437 base pairs
        (B) TYPE: nucleic acid
        (C) STRANDEDNESS: single
        (D) TOPOLOGY: linear (xi) SEQUENCE DESCRIPTION: SEQ ID NO: 9:

```
AAGTTCAGTG CCTACCGAAG ACAAAGGCGC CCCGAGGGAG TGGCGGTGCG A CCCCAGGGC      60

GTGGGCCCGG CCGCGGAGCC CACACTGCCC GGCTGACCCG GTGGTCTCGG A CCATGTCTC     120

CCGCCCCAAG ACCCCCCCGT TGTCTCCTGC TCCCCCTGCT CACGCTCGGC A CCGCGCTCG     180

CCTCCCTCGG CTCGGCCCAA AGCAGCAGCT TCAGCCCCGA AGCCTGGCTA C AGCAATATG     240

GCTACCTGCC TCCCGGGGAC CTACGTACCC ACACACAGCG CTCACCCCAG T CACTCTCAG     300

CGGCCATCGC TGCCATGCAG AAGTTTTACG GCTTGCAAGT AACAGGCAAA G CTGATGCAG     360

ACACCATGAA GGCCATGAGG CGCCCCCGAT GTGGTGTTCC AGACAAGTTT G GGGCTGAGA     420

TCAAGGCCAA TGTTCGAAGG AAGCGCTACG CCATCCAGGG TCTCAAATGG C AACATAATG     480

AAATCACTTT CTGCATCCAG AATTACACCC CCAAGGTGGG CGAGTATGCC A CATACGAGG     540

CCATTCGCAA GGCGTTCCGC GTGTGGGAGA GTGCCACACC ACTGCGCTTC C GCGAGGTGC     600

CCTATGCCTA CATCCGTGAG GGCCATGAGA AGCAGGCCGA CATCATGATC T TCTTTGCCG     660

AGGGCTTCCA TGGCGACAGC ACGCCCTTCG ATGGTGAGGG CGGCTTCCTG G CCCATGCCT     720

ACTTCCCAGG CCCCAACATT GGAGGAGACA CCCACTTTGA CTCTGCCGAG C TTGGACTGG     780

TCAGGAATGA GGATCTGAAT GGAAATGACA TCTTCCTGGT GGCTGTGCAC G AGCTGGGCC     840

ATGCCCTGGG GCTCGAGCAT TCCAGTGACC CCTCGGCCAT CATGGCACCC T TTTACCAGT     900

GGATGGACAC GGAGAATTTT GTGCTGCCCG ATGATGACCG CCGGGGCATC C AGCAACTTT     960

ATGGGGGTGA GTCAGGGTTC CCCACCAAGA TGCCCCCTCA ACCCAGGACT A CCTCCCGGC    1020

CTTCTGTTCC TGATAAACCC AAAAACCCCA CCTATGGGCC CAACATCTGT G ACGGGAACT    1080

TTGACACCGT GGCCATGCTC CGAGGGGAGA TGTTTGTCTT CAAGGAGCGC T GGTTCTGGC    1140

GGGTGAGGAA TAACCAAGTG ATGGATGGAT ACCCAATGCC CATTGGCCAG T TCTGGCGGG    1200

GCCTGCCTGC GTCCATCAAC ACTGCCTACG AGAGGAAGGA TGGCAAATTC G TCTTCTTCA    1260

AAGGAGACAA GCATTGGGTG TTTGATGAGG CGTCCCTGGA ACCTGGCTAC C CCAAGCACA    1320

TTAAGGAGCT GGGCCGAGGG CTGCCTACCG ACAAGATTGA TGCTGCTCTC T TCTGGATGC    1380

CCAATGGAAA GACCTACTTC TTCCGTGGAA ACAAGTACTA CCGTTTCAAC G AAGAGCTCA    1440

GGGCAGTGGA TAGCGAGTAC CCCAAGAACA TCAAAGTCTG GAAGGGATCC C TGAGTCTCC    1500

CCAGAGGGTC ATTCATGGGC AGCGATGAAG TCTTCACTTA CTTCTACAAG G GAACAAAT    1560

ACTGGAAATT CAACAACCAG AAGCTGAAGG TAGAACCGGG CTACCCCAAG T CAGCCCTGA    1620

GGGACTGGAT GGGCTGCCCA TCGGGAGGCC GGCCGGATGA GGGGACTGAG G AGGAGACGG    1680

AGGTGATCAT CATTGAGGTG GACGAGGAGG GCGGCGGGGC GGTGAGCGCG G CTGCCGTGG    1740
```

-continued

```
TGCTGCCCGT GCTGCTGCTG CTCCTGGTGC TGGCGGTGGG CCTTGCAGTC T TCTTCTTCA    1800

GACGCCATGG GACCCCCAGG CGACTGCTCT ACTGCCAGCG TTCCCTGCTG G ACAAGGTCT    1860

GACGCCCACC GCCGGCCCGC CCACTCCTAC CACAAGGACT TTGCCTCTGA A GGCCAGTGG    1920

CAGCAGGTGG TGGTGGGTGG GCTGCTCCCA TCGTCCCGAG CCCCCTCCCC G CAGCCTCCT    1980

TGCTTCTCTC TGTCCCCTGG CTGGCCTCCT TCACCCTGAC CGCCTCCCTC C CTCCTGCCC    2040

CGGCATTGCA TCTTCCCTAG ATAGGTCCCC TGAGGGCTGA GTGGGAGGGC G GCCCTTTCC    2100

AGCCTCTGCC CCTCAGGGGA ACCCTGTAGC TTTGTGTCTG TCCAGCCCCA T CTGAATGTG    2160

TTGGGGGCTC TGCACTTGAA GGCAGGACCC TCAGACCTCG CTGGTAAAGG T CAAATGGGG    2220

TCATCTGCTC CTTTTCCATC CCCTGACATA CCTTAACCTC TGAACTCTGA C CTCAGGAGG    2280

CTCTGGGCAC TCCAGCCCTG AAAGCCCCAG GTGTACCCAA TTGGCAGCCT C TCACTACTC    2340

TTTCTGGCTA AAAGGAATCT AATCTTGTTG AGGGTAGAGA CCCTGAGACA G TGTGAGGGG    2400

GTGGGGACTG CCAAGCCACC CTAAGACCTT GGGAGGAAAA CTCAGAGAGG G TCTTCGTTG    2460

CTCAGTCAGT CAAGTTCCTC GGAGATCTGC CTCTGCCTCA CCTACCCCAG G GAACTTCCA    2520

AGGAAGGAGC CTGAGCCACT GGGGACTAAG TGGGCAGAAG AAACCCTTGG C AGCCCTGTG    2580

CCTCTCGAAT GTTAGCCTTG GATGGGCTT TCACAGTTAG AAGAGCTGAA A CCAGGGGTG    2640

CAGCTGTCAG GTAGGGTGGG GCCGGTGGGA GAGGCCCGGG TCAGAGCCCT G GGGGTGAGC    2700

CTGAAGGCCA CAGAGAAAGA ACCTTGCCCA AACTCAGGCA GCTGGGGCTG A GGCCCAAAG    2760

GCAGAACAGC CAGAGGGGGC AGGAGGGGAC CAAAAAGGAA AATGAGGACG T GCAGCAGCA    2820

TTGGAAGGCT GGGGCCGGGC AGGCCAGGCC AAGCCAAGCA GGGGGCCACA G GGTGGGCTG    2880

TGGAGCTCTC AGGAAGGGCC CTGAGGAAGG CACACTTGCT CCTGTTGGTC C CTGTCCTTG    2940

CTGCCCAGGC AGCGTGGAGG GGAAGGGTAG GGCAGCCAGA GAAAGGAGCA G AGAAGGCAC    3000

ACAAACGAGG AATGAGGGGC TTCACGAGAG CCCACAGGGC CTGGCTGGCC A CGCTGTCCC    3060

GGCCTGCTCA CCATCTCAGT GAGGGCAGG AGCTGGGGCT CGCTTAGGCT G GGTCCACGC    3120

TTCCCTGGTG CCAGCACCCC TCAAGCCTGT CTCACCAGTG GCCTGCCCTC T CGCTCCCCC    3180

ACCCAGCCCA CCCATTGAAG TCTCCTTGGG CCACCAAAGG TGGTGGCCAT G GTACCGGGG    3240

ACTTGGGAGA GTGAGACCCA GTGGAGGGAG CAAGAGGAGA GGGATGTCGG G GGGTGGGG    3300

CACGGGGTAG GGGAAATGGG GTGAACGGTG CTGGCAGTTC GGCTAGATTT C TGTCTTGTT    3360

TGTTTTTTTG TTTTGTTTAA TGTATATTTT TATTATAATT ATTATATATG A ATTCCAAAA    3420

AAAAAAAAAA AAAAAAA                                                    3437
```

(2) INFORMATION FOR SEQ ID NO: 10:

(i) SEQUENCE CHARACTERISTICS:
        (A) LENGTH: 3530 base pairs
        (B) TYPE: nucleic acid
        (C) STRANDEDNESS: single
        (D) TOPOLOGY: linear (xi) SEQUENCE DESCRIPTION: SEQ ID NO: 10:

```
GCGAGGATCC GGCGTGCAGT GTTCCGAGCT GGGCTGGGCG CCGAGAGCAT G GGCAGCGAC     60

CCGAGCGCGC CCGGACGGCC GGGCTGGACG GGCAGCCTCC TCGGCGACCG G GAGGAGGCG    120

GCGCGGCCGC GACTGCTGCC GCTGCTCCTG GTGCTTCTGG GCTGCCTGGG C CTTGGCGTA    180

GCGGCCGAAG ACGCGGAGGT CCATGCCGAG AACTGGCTGC GGCTTTATGG C TACCTGCCT    240

CAGCCCAGCC GCCATATGTC CACCATGCGT TCCGCCCAGA TCTTGGCCTC G GCCCTTGCA    300
```

-continued

```
GAGATGCAGC GCTTCTACGG GATCCCAGTC ACCGGTGTGC TCGACGAAGA G ACCAAGGAG    360

TGGATGAAGC GGCCCCGCTG TGGGGTGCCA GACCAGTTCG GGGTACGAGT G AAAGCCAAC    420

CTGCGGCGGC GTCGGAAGCG CTACGCCCTC ACCGGGAGGA AGTGGAACAA C CACCATCTG    480

ACCTTTAGCA TCCAGAACTA CACGGAGAAG TTGGGCTGGT ACCACTCGAT G GAGGCGGTG    540

CGCAGGGCCT TCCGCGTGTG GGAGCAGGCC ACGCCCCTGG TCTTCCAGGA G GTGCCCTAT    600

GAGGACATCC GGCTGCGGCG ACAGAAGGAG GCCGACATCA TGGTACTCTT T GCCTCTGGC    660

TTCCACGGCG ACAGCTCGCC GTTTGATGGC ACCGGTGGCT TTCTGGCCCA C GCCTATTTC    720

CCTGGCCCCG GCCTAGGCGG GGACACCCAT TTTGACGCAG ATGAGCCCTG G ACCTTCTCC    780

AGCACTGACC TGCATGGAAA CAACCTCTTC CTGGTGGCAG TGCATGAGCT G GCCACGCGC    840

CTGGGGCTGG AGCACTCCAG CAACCCCAAT GCCATCATGG CGCCGTTCTA C CAGTGGAAG    900

GACGTTGACA ACTTCAAGCT GCCCGAGGAC GATCTCCGTG GCATCCAGCA G CTCTACGGT    960

ACCCCAGACG GTCAGCCACA GCCTACCCAG CCTCTCCCCA CTGTGACGCC A CGGCGGCCA    1020

GGCCGGCCTG ACCACCGGCC GCCCCGGCCT CCCCAGCCAC CACCCCCAGG T GGGAAGCCA    1080

GAGCGGCCCC CAAAGCCGGG CCCCCCAGTC CAGCCCCGAG CCACAGAGCG G CCCGACCAG    1140

TATGGCCCCA ACATCTGCGA CGGGGACTTT GACACAGTGG CCATGCTTCG C GGGGAGATG    1200

TTCGTGTTCA AGGGCCGCTG GTTCTGGCGA GTCCGGCACA ACCGCGTCCT G GACAACTAT    1260

CCCATGCCCA TCGGGCACTT CTGGCGTGGT CTGCCCGGTG ACATCAGTGC T GCCTACGAG    1320

CGCCAAGACG GTCGTTTTGT CTTTTTCAAA GGTGACCGCT ACTGGCTCTT T CGAGAAGCG    1380

AACCTGGAGC CCGGCTACCC ACAGCCGCTG ACCAGCTATG GCCTGGGCAT C CCCTATGAC    1440

CGCATTGACA CGGCCATCTG GTGGGAGCCC ACAGGCCACA CCTTCTTCTT C CAAGAGGAC    1500

AGGTACTGGC GCTTCAACGA GGAGACACAG CGTGGAGACC CTGGGTACCC C AAGCCCATC    1560

AGTGTCTGGC AGGGGATCCC TGCCTCCCCT AAAGGGGCCT TCCTGAGCAA T GACGCAGCC    1620

TACACCTACT TCTACAAGGG CACCAAATAC TGGAAATTCG ACAATGAGCG C CTGCGGATG    1680

GAGCCCGGCT ACCCCAAGTC CATCCTGCGG GACTTCATGG GCTGCCAGGA G CACGTGGAG    1740

CCAGGCCCCC GATGGCCCGA CGTGGCCCGG CCGCCCTTCA ACCCCCACGG G GGTGCAGAG    1800

CCCGGGGCGA CAGCGCAGA GGGCGACGTG GGGGATGGGG ATGGGGACTT T GGGGCCGGG    1860

GTCAACAAGG ACGGGGCAG CCGCGTGGTG GTGCAGATGG AGGAGGTGGC A CGGACGGTG    1920

AACGTGGTGA TGGTGCTGGT GCCACTGCTG CTGCTGCTCT GCGTCCTGGG C CTCACCTAC    1980

GCGCTGGTGC AGATGCAGCG CAAGGGTGCG CCACGTGTCC TGCTTTACTG C AAGCGCTCG    2040

CTGCAGGAGT GGGTCTGACC ACCCAGCGCT CCTGCTAACG GTGCTCAGGG G GCGCCTGTG    2100

GTTCTGAGAT GGCTCCCAGG GGCTCCCTCC GCCCCAGGT AGGGGCCCCT C TCAGCCCTC    2160

ACACACCCTG TCTGCCCCGC CCTCATTATT TATGTCCAGG TGTTTGTTTT G TTTTGTTTT    2220

TGGCACCTTA CTTGACCATT TGTTTCTGTT TCCCCGACTG GGGCAGGGTG T TTAGAATTT    2280

TCTAAATGTA GTTCTGCTCC AGACAGGGAA TTAGGCCCCC ATCATCCTCT G GCTTGGCCA    2340

CAGCCAGGGG AGCAGAGGGG CAGAGGCCCA CATTGGAAGA GCAGCACCTC C TCAGCCTGA    2400

ACCCCAGGGC TGTAACTGCC AGGCTCTCTT TGCCCAGTTG GAGACTGTCT G GCCCCCCTG    2460

GTCCCCTCCT TCCCAAGTGA GTCTCTCTGG GCCTTAGGAA GAGCCTTCCA C CCAGGGGCA    2520

GCCCCAGGCC AAAGGGGACC TGGAAGGGAG GTGGGCCGTG GCCCTTGAGT C CCCATTGAG    2580

GCTTGGTTCC TTCCCAATCC AGTGGACTTC GCAGTCCACT TCTGACAGCC T CAGTGACCC    2640

TGGCTCCTTG TGCCAGAGAA CCCAGCCCAC CCCCGGCAGC AGCCCCCAGC T CCCACCTCC    2700
```

```
CCTTGGGCCC ACACCTTCTT CCCTCTCTGG AGAAAGGGCC CTGGGCCTGC C TCACCACGG    2760

ACCAAAGGGA GTCTGCCAGG GCCCCTCTCC CCAGGGAAGC AGCAGCCTCG C CCCTGGCAG    2820

AGATGCCTCC CTGAGCTAGA ACCCTCTGTT CCTTCCCTGT GCCTCCTCCC T CCCTCCCGA    2880

CTCACACCAC TAGCCTCAGG GGTCTGAGCT CCAGCTCCTT TGGGCTTCAG C TGCCAGTGT    2940

CCTGAGCCCC AGGGAGAGGG GGCTGGTGGG TGCCTAGGCC TGGGCAGTGG A TGGCCGTGA    3000

ATGGGTGCCC ACAGTGTCAG GCACTGGGCA TGAGGGGTTC CTCCCCTCCA G CTCCCTGTG    3060

CCCCCAGGGT CCTGGGAGGA GAGACACTGG TGGGGATAGG CCAGCCGCGC A TCAGACTGT    3120

GAACCCCACG AAGGAGCCCA TTGTGGCCTA AGAGGCTGCC CTCCTGTGCT C AGCCCTGAG    3180

GACAGATGCC TCCTTCCTCT TTTCCTTCCC AAAGCAAGCA AGAGGCCGTG G CTGCTGTGG    3240

GAAATGGTAC TGTACAGCTG GCTCTACTTC CCCATGGCCC TGAGCGAGTG G AGTCTGCCA    3300

CCCAGGATCC CCAAGGCACT TGAGGGGGAA GGATTCTGCT GGCCTCTGCG A GTGGTTTCT    3360

TGTGCACTGG CACCAAGTGC GGGTCCGGCA GCTTCTGCCC CCTGCAGAAC C GGAGAGCCA    3420

GCTAAGGGGT GGGGCTGCGG GGGTTCCGTG TCCACCCCCA TACATTTATT T CTGTAAATA    3480

ATGTGCACTG AATAAATTGT ACAGCCGGCA AAAAAAAAA AAAAAAAAA              3530

(2) INFORMATION FOR SEQ ID NO: 11:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 11:

Pro Arg Cys Gly Val Pro Asp
1               5

(2) INFORMATION FOR SEQ ID NO: 12:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 12:

Arg Arg Lys Arg Tyr Ala
1               5

(2) INFORMATION FOR SEQ ID NO: 13:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO: 13:

His Glu Leu Gly His Ala Leu Gly Leu Glu H is
1               5                   10

(2) INFORMATION FOR SEQ ID NO: 14:

(i) SEQUENCE CHARACTERISTICS:
        (A) LENGTH: 472 base pairs
        (B) TYPE: nucleic acid
        (C) STRANDEDNESS: single
        (D) TOPOLOGY: linear
```

(xi) SEQUENCE DESCRIPTION: SEQ ID NO: 14:

```
TCTAGACCCA GGTGCGGGGT GCCGGACAAG TTTGGGGCTG AGATCAAGGC C AATGTTCGA      60

AGGAAGCGCT ACGCCATCCA GGGTCTCAAA TGGCAACATA ATGAAATCAC T TTCTGCATC     120

CAGAATTACG CGCCCAAGGT GGGCGAGTAT GCCACATACG AGGCCATTCG C AAGGCGTTC     180

CGCATGTGGG AGAGTGCCAC ACCACTGCGC TTGCGCGAGG TGCCCTATGC C TACATCCGT     240

GAGGCCATGA GAAGCAGGCC GACATCATGA TCTTCTTTGC CGAGGGTTCC A TGGCGACAG     300

CGCCCTTCGA TGGTGAGGGC GGCTTCCTGG CCCGTGCCTA CTTCCCAGGC C CCAACATTG     360

GAGGAGACAC CCACTTTGAC TCTGCCGAGC CTTGGACTGT CAGGAATGAG G ATCTGAATG     420

GAAATACATC TTCCTGGTGG CTGTGCACGA ACTCGGCCAC CGCTGGGGAT C C            472
```

(2) INFORMATION FOR SEQ ID NO: 15:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (xi) SEQUENCE DESCRIPTION: SEQ ID NO: 15:

```
TCTAGACCCA GGTGCGGGAA GCCGGACCAG TTCGGGGTAC GAGTGAAAGC C AACCTGCGG      60

CGGCGTCGGA AGCGCTACGC CCTCACCGGG AGGAAGTGGA ATAACCAACC A TCTGACCTT     120

TAGCATCCAG AACTACACCG GAGAAGTTGG GCTGGTACCA CTCGATGGAG G CGGTGCGCA     180

GGGCCTTCCG CGTGTGGGAG CAGGCCACGC CCCTGGTCTT CCAGGAGGTG C CCTATGAGA     240

CATCCGGCTG CGGCGACAGA AGGAGGCCGA CATCATGGTA CTCTTTCCCT C TGGCTTCCA     300

CGGCGAACAG CTCGCCGTTT GATGGCACCG GTGGCTTTCT GGCCCACGCC T ATTTCCCTG     360

GCCCCGGCCT AGGCGGGGAC ACCCATTTTG ACGCAGATGA GCCCTGGACC T TCTCCAGCA     420

CTGACCTGCA TGGAAACAAC CTCTTCCTGG TGGCAGTGCA TGAGCTGGGC C ACGCGCTGG     480

GGGATCC                                                               487
```

(2) INFORMATION FOR SEQ ID NO: 16:

(i) SEQUENCE CHARACTERISTICS:
        (A) LENGTH: 469 amino acids
        (B) TYPE: amino acid
        (C) STRANDEDNESS: single
        (D) TOPOLOGY: linear (xi) SEQUENCE DESCRIPTION: SEQ ID NO: 16:

```
Met His Ser Phe Pro Pro Leu Leu Leu L eu Phe Trp Gly Val Val
1               5                  10                  15

Ser His Ser Phe Pro Ala Thr Leu Glu Thr G ln Glu Gln Asp Val Asp
               20                  25                  30

Leu Val Gln Lys Tyr Leu Glu Lys Tyr Tyr A sn Leu Lys Asn Asp Gly
               35                  40                  45

Arg Gln Val Glu Lys Arg Arg Asn Ser Gly P ro Val Val Glu Lys Leu
               50                  55                  60

Lys Gln Met Gln Glu Phe Phe Gly Leu Lys V al Thr Gly Lys Pro Asp
65                  70                  75                  80

Ala Glu Thr Leu Lys Val Met Lys Gln Pro A rg Cys Gly Val Pro Asp
               85                  90                  95

Val Ala Gln Phe Val Leu Thr Glu Gly Asn P ro Arg Trp Glu Gln Thr
               100                 105                 110
```

```
His Leu Thr Tyr Arg Ile Glu Asn Tyr Thr Pro Asp Leu Pro Arg Ala
        115                 120                 125

Asp Val Asp His Ala Ile Glu Lys Ala Phe Gln Leu Trp Ser Asn Val
130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
            180                 185                 190

Gly Asp Ala His Phe Asp Glu His Glu Arg Trp Thr Asn Asn Phe Thr
        195                 200                 205

Glu Tyr Asn Leu His Arg Val Ala Ala His Glu Leu Gly His Ser Leu
        210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
            260                 265                 270

Gln Thr Pro Lys Ala Cys Asp Ser Lys Leu Thr Phe Asp Ala Ile Thr
        275                 280                 285

Thr Ile Arg Gly Glu Val Met Phe Phe Lys Asp Arg Phe Tyr Met Arg
        290                 295                 300

Thr Asn Pro Phe Tyr Pro Glu Val Glu Leu Asn Phe Thr Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
            340                 345                 350

Gly Gln Asn Val Leu His Gly Tyr Pro Lys Asp Ile Tyr Ser Ser Phe
        355                 360                 365

Gly Phe Pro Arg Thr Val Lys His Ile Asp Ala Ala Leu Ser Glu Glu
        370                 375                 380

Asn Thr Gly Lys Thr Tyr Phe Phe Val Ala Asn Lys Tyr Trp Arg Tyr
385                 390                 395                 400

Asp Glu Tyr Lys Arg Ser Met Asp Pro Gly Tyr Pro Lys Met Ile Ala
                405                 410                 415

His Asp Phe Pro Gly Ile Gly His Lys Val Asp Ala Val Phe Met Lys
            420                 425                 430

Asp Gly Phe Phe Tyr Phe Phe His Gly Thr Arg Gln Tyr Lys Phe Asp
        435                 440                 445

Pro Lys Thr Lys Arg Ile Leu Thr Leu Gln Lys Ala Asn Ser Trp Phe
        450                 455                 460

Asn Cys Arg Lys Asn
465
```

(2) INFORMATION FOR SEQ ID NO: 17:

(i) SEQUENCE CHARACTERISTICS:
        (A) LENGTH: 466 amino acids
        (B) TYPE: amino acid
        (C) STRANDEDNESS: single
        (D) TOPOLOGY: linear -continued (xi) SEQUENCE DESCRIPTION: SEQ ID NO: 17:

```
Met Phe Ser Leu Lys Thr Leu Pro Phe Leu Leu Leu Leu His Val Gln
1               5                   10                  15

Ile Ser Lys Ala Phe Pro Val Ser Ser Lys Glu Lys Asn Thr Lys Thr
                20                  25                  30

Val Gln Asp Tyr Leu Glu Lys Phe Tyr Gln Leu Pro Ser Asn Gln Tyr
            35                  40                  45

Gln Ser Thr Arg Lys Asn Gly Thr Asn Val Ile Val Glu Lys Leu Lys
        50                  55                  60

Glu Met Gln Arg Phe Phe Gly Leu Asn Val Thr Gly Lys Pro Asn Glu
65                  70                  75                  80

Glu Thr Leu Asp Met Met Lys Lys Pro Arg Cys Gly Val Pro Asp Ser
                85                  90                  95

Gly Gly Phe Met Leu Thr Pro Gly Asn Pro Lys Trp Glu Arg Thr Asn
                100                 105                 110

Leu Thr Tyr Arg Ile Arg Asn Tyr Thr Pro Gln Leu Ser Glu Ala Glu
            115                 120                 125

Val Glu Arg Ala Ile Lys Asp Ala Phe Glu Leu Trp Ser Val Ala Ser
        130                 135                 140

Pro Leu Ile Phe Thr Arg Ile Ser Gln Gly Glu Ala Asp Ile Asn Ile
145                 150                 155                 160

Ala Phe Tyr Gln Arg Asp His Gly Asp Asn Ser Pro Phe Asp Gly Pro
                165                 170                 175

Asn Gly Ile Leu Ala His Ala Phe Gln Pro Gly Gln Gly Ile Gly Gly
                180                 185                 190

Asp Ala His Phe Asp Ala Glu Glu Thr Trp Thr Asn Thr Ser Ala Asn
            195                 200                 205

Tyr Asn Leu Phe Leu Val Ala Ala His Glu Phe Gly His Ser Leu Gly
        210                 215                 220

Leu Ala His Ser Ser Asp Pro Gly Ala Leu Met Tyr Pro Asn Tyr Ala
225                 230                 235                 240

Phe Arg Glu Thr Ser Asn Tyr Ser Leu Pro Gln Asp Asp Ile Asp Gly
                245                 250                 255

Ile Gln Ala Ile Tyr Gly Leu Ser Ser Asn Pro Ile Gln Pro Thr Gly
                260                 265                 270

Pro Ser Thr Pro Lys Pro Cys Asp Pro Ser Leu Thr Phe Asp Ala Ile
            275                 280                 285

Thr Thr Leu Arg Gly Glu Ile Leu Phe Phe Lys Asp Arg Tyr Phe Trp
290                 295                 300

Arg Arg His Pro Gln Leu Gln Arg Val Glu Met Asn Phe Ile Ser Leu
305                 310                 315                 320

Phe Trp Pro Ser Leu Pro Thr Gly Ile Gln Ala Ala Tyr Glu Asp Phe
                325                 330                 335

Asp Arg Asp Leu Ile Phe Leu Phe Lys Gly Asn Gln Tyr Trp Ala Leu
            340                 345                 350

Ser Gly Tyr Asp Ile Leu Gln Gly Tyr Pro Lys Asp Ile Ser Asn Tyr
        355                 360                 365

Gly Phe Pro Ser Ser Val Gln Ala Ile Asp Ala Ala Val Phe Tyr Arg
        370                 375                 380

Ser Lys Thr Tyr Phe Phe Val Asn Asp Gln Phe Trp Arg Tyr Asp Asn
385                 390                 395                 400

Gln Arg Gln Phe Met Glu Pro Gly Tyr Pro Lys Ser Ile Ser Gly Ala
                405                 410                 415
```

```
Phe Pro Gly Ile Glu Ser Lys Asp Ala Val Phe Gln Gln Glu His Phe
            420                 425                 430

Phe His Val Phe Ser Gly Pro Arg Tyr Tyr Ala Phe Asp Leu Ile Ala
            435                 440                 445

Gln Arg Val Thr Arg Val Ala Arg Gly Asn Lys Trp Leu Asn Cys Arg
450                 455                 460

Tyr Gly
465

(2) INFORMATION FOR SEQ ID NO: 18:

(i) SEQUENCE CHARACTERISTICS:
        (A) LENGTH: 660 amino acids
        (B) TYPE: amino acid
        (C) STRANDEDNESS: single
        (D) TOPOLOGY: linear (xi) SEQUENCE DESCRIPTION: SEQ ID NO: 18:

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Ala Phe Ser
            20                  25                  30

Pro Ile Ile Lys Phe Pro Gly Asp Val Ala Pro Lys Thr Asp Lys Glu
        35                  40                  45

Leu Ala Val Gln Tyr Leu Asn Thr Phe Tyr Gly Cys Pro Lys Glu Ser
50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
            85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
        115                 120                 125

Ile Gly Tyr Thr Pro Asp Leu Asp Pro Glu Thr Val Asp Asp Ala Phe
    130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
    210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
        275                 280                 285

Gln Pro Cys Lys Phe Pro Phe Arg Phe Gln Gly Thr Ser Tyr Asp Ser
    290                 295                 300
```

```
Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
            325                 330                 335

Met Ser Thr Val Gly Gly Asn Ser Glu Gly Ala Pro Cys Val Phe Pro
                340                 345                 350

Phe Thr Phe Leu Gly Asn Lys Tyr Glu Ser Cys Thr Ser Ala Gly Arg
            355                 360                 365

Ser Asp Gly Lys Met Trp Cys Ala Thr Ala Asn Tyr Asp Asp Asp
370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
                420                 425                 430

Leu Ser Gln Asp Asp Ile Lys Gly Ile Gln Glu Leu Tyr Gly Ala Ser
            435                 440                 445

Pro Asp Ile Asp Leu Gly Thr Gly Pro Thr Pro Thr Leu Gly Pro Val
450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
                485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
515                 520                 525

Glu Glu Lys Ala Val Phe Phe Ala Gly Asn Glu Tyr Trp Ile Tyr Ser
530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
610                 615                 620

Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
            645                 650                 655

Trp Leu Gly Cys
            660

(2) INFORMATION FOR SEQ ID NO: 19:

(i) SEQUENCE CHARACTERISTICS:
        (A) LENGTH: 707 amino acids
        (B) TYPE: amino acid
        (C) STRANDEDNESS: single
        (D) TOPOLOGY: linear
```

(xi) SEQUENCE DESCRIPTION: SEQ ID NO: 19:

```
Met Ser Leu Trp Gln Pro Leu Val Leu Val Leu Val Leu Gly Cys
 1               5                  10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
                35                  40                  45

Leu Tyr Arg Tyr Gly Tyr Thr Arg Val Ala Glu Met Arg Gly Glu Ser
50                  55                  60

Lys Ser Leu Gly Pro Ala Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
                100                 105                 110

Asp Leu Lys Trp His His His Asn Ile Thr Tyr Trp Ile Gln Asn Tyr
                115                 120                 125

Ser Glu Asp Leu Pro Arg Ala Val Ile Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
                180                 185                 190

Pro Pro Gly Pro Gly Ile Gln Gly Asp Ala His Phe Asp Asp Asp Glu
                195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
                260                 265                 270

Ser Glu Arg Leu Tyr Thr Arg Asp Gly Asn Ala Asp Gly Lys Pro Cys
                275                 280                 285

Gln Phe Pro Phe Ile Phe Gln Gly Gln Ser Tyr Ser Ala Cys Thr Thr
                290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
                340                 345                 350

Phe Leu Gly Lys Glu Tyr Ser Thr Cys Thr Ser Glu Gly Arg Gly Asp
                355                 360                 365

Gly Arg Leu Trp Cys Ala Thr Thr Ser Asn Phe Asp Ser Asp Lys Lys
                370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415
```

```
Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Thr Thr Thr Pro Gln Pro Thr Ala Pro
    450                 455                 460

Pro Thr Val Cys Pro Thr Gly Pro Pro Val His Pro Ser Glu Arg
465                 470                 475                 480

Pro Thr Ala Gly Pro Thr Gly Pro Pro Ser Ala Gly Pro Thr Gly Pro
            485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
        530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
            565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
            595                 600                 605

Asp Val Ala Gln Val Thr Gly Ala Leu Arg Ser Gly Arg Gly Lys Met
        610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
            645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705

(2) INFORMATION FOR SEQ ID NO: 20:

(i) SEQUENCE CHARACTERISTICS:
        (A) LENGTH: 477 amino acids
        (B) TYPE: amino acid
        (C) STRANDEDNESS: single
        (D) TOPOLOGY: linear (xi) SEQUENCE DESCRIPTION: SEQ ID NO: 20:

Met Lys Ser Leu Pro Ile Leu Leu Leu Cys Val Ala Val Cys Ser
1               5                   10                  15

Ala Tyr Pro Leu Asp Gly Ala Ala Arg Gly Glu Asp Thr Ser Met Asn
            20                  25                  30

Leu Val Gln Lys Tyr Leu Glu Asn Tyr Tyr Asp Leu Glu Lys Asp Val
        35                  40                  45

Lys Gln Phe Val Arg Arg Lys Asp Ser Gly Pro Val Val Lys Lys Ile
    50                  55                  60
```

-continued

```
Arg Glu Met Gln Lys Phe Leu Gly Leu Glu Val Thr Gly Lys Leu Asp
 65                  70                  75                  80

Ser Asp Thr Leu Glu Val Met Arg Lys Pro Arg Cys Gly Val Pro Asp
                 85                  90                  95

Val Gly His Phe Arg Thr Phe Pro Gly Ile Pro Lys Trp Arg Lys Thr
            100                 105                 110

His Leu Thr Tyr Arg Ile Val Asn Tyr Thr Pro Asp Leu Pro Lys Asp
        115                 120                 125

Ala Val Asp Ser Ala Val Glu Lys Ala Leu Lys Val Trp Glu Glu Val
130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
                165                 170                 175

Pro Gly Asn Val Leu Ala His Ala Tyr Ala Pro Gly Pro Gly Ile Asn
            180                 185                 190

Gly Asp Ala His Phe Asp Asp Asp Glu Gln Trp Thr Lys Asp Thr Thr
        195                 200                 205

Gly Thr Asn Leu Phe Leu Val Ala Ala His Glu Ile Gly His Ser Leu
210                 215                 220

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
                245                 250                 255

Asn Gly Ile Gln Ser Leu Tyr Gly Pro Pro Pro Asp Ser Pro Glu Thr
            260                 265                 270

Pro Leu Val Pro Thr Glu Pro Val Pro Pro Glu Pro Gly Thr Pro Ala
        275                 280                 285

Asn Cys Asp Pro Ala Leu Ser Phe Asp Ala Val Ser Thr Leu Arg Gly
290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
                325                 330                 335

Pro Ser Gly Val Asp Ala Ala Tyr Glu Val Thr Ser Lys Asp Leu Val
            340                 345                 350

Phe Ile Phe Lys Gly Asn Gln Phe Trp Ala Ile Arg Gly Asn Glu Val
        355                 360                 365

Arg Ala Gly Tyr Pro Arg Gly Ile His Thr Leu Gly Phe Pro Pro Thr
370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
                405                 410                 415

Ser Met Glu Pro Gly Phe Pro Lys Gln Ile Ala Glu Asp Phe Pro Gly
            420                 425                 430

Ile Asp Ser Lys Ile Asp Ala Val Phe Glu Phe Gly Phe Phe Phe Tyr
        435                 440                 445

Phe Phe Thr Gly Ser Ser Gln Leu Glu Phe Asp Pro Asn Ala Lys Lys
450                 455                 460

Val Thr His Thr Leu Lys Ser Asn Ser Trp Leu Asn Cys
465                 470                 475
```

-continued (2) INFORMATION FOR SEQ ID NO: 21:

(i) SEQUENCE CHARACTERISTICS:
(A) LENGTH: 476 amino acids
(B) TYPE: amino acid
(C) STRANDEDNESS: single
(D) TOPOLOGY: linear (xi) SEQUENCE DESCRIPTION: SEQ ID NO: 21:

```
Met Met His Leu Ala Phe Leu Val Leu Leu Cys Leu Pro Val Cys Ser
  1               5                  10                  15

Ala Tyr Pro Leu Ser Gly Ala Ala Lys Glu Glu Asp Ser Asn Lys Asp
             20                  25                  30

Leu Ala Gln Gln Tyr Leu Glu Lys Tyr Tyr Asn Leu Glu Lys Asp Val
         35                  40                  45

Lys Gln Phe Arg Arg Lys Asp Ser Asn Leu Ile Val Lys Lys Ile Gln
 50                  55                  60

Gly Met Gln Lys Phe Leu Gly Leu Glu Val Thr Gly Lys Leu Asp Thr
 65                  70                  75                  80

Asp Thr Leu Glu Val Met Arg Lys Pro Arg Cys Gly Val Pro Asp Val
                 85                  90                  95

Gly His Phe Ser Ser Phe Pro Gly Met Pro Lys Trp Arg Lys Thr His
            100                 105                 110

Leu Thr Tyr Arg Ile Val Asn Tyr Thr Pro Asp Leu Pro Arg Asp Ala
        115                 120                 125

Val Asp Ser Ala Ile Glu Lys Ala Leu Lys Val Trp Glu Glu Val Thr
130                 135                 140

Pro Leu Thr Phe Ser Arg Leu Tyr Glu Gly Glu Ala Asp Ile Met Ile
145                 150                 155                 160

Ser Phe Ala Val Lys Glu His Gly Asp Phe Tyr Ser Phe Asp Gly Pro
                165                 170                 175

Gly His Ser Leu Ala His Ala Tyr Pro Gly Pro Gly Leu Tyr Gly
            180                 185                 190

Asp Ile His Phe Asp Asp Asp Glu Lys Trp Thr Glu Asp Ala Ser Gly
        195                 200                 205

Thr Asn Leu Phe Leu Val Ala Ala His Glu Leu Gly His Ser Leu Gly
210                 215                 220

Leu Phe His Ser Ala Asn Thr Glu Ala Leu Met Tyr Pro Leu Tyr Asn
225                 230                 235                 240

Ser Phe Thr Glu Leu Ala Gln Phe Arg Leu Ser Gln Asp Asp Val Asn
                245                 250                 255

Gly Ile Gln Ser Leu Tyr Gly Pro Pro Pro Ala Ser Thr Glu Glu Pro
            260                 265                 270

Leu Val Pro Thr Lys Ser Val Pro Ser Gly Ser Glu Met Pro Ala Lys
        275                 280                 285

Cys Asp Pro Ala Leu Ser Phe Asp Ala Ile Ser Thr Leu Arg Gly Glu
290                 295                 300

Tyr Leu Phe Phe Lys Asp Arg Tyr Phe Trp Arg Arg Ser His Trp Asn
305                 310                 315                 320

Pro Glu Pro Glu Phe His Leu Ile Ser Ala Phe Trp Pro Ser Leu Pro
                325                 330                 335

Ser Tyr Leu Asp Ala Ala Tyr Glu Val Asn Ser Arg Asp Thr Val Phe
            340                 345                 350

Ile Phe Lys Gly Asn Glu Phe Trp Ala Ile Arg Gly Asn Glu Val Gln
        355                 360                 365
```

```
Ala Gly Tyr Pro Arg Gly Ile His Thr Leu Gly Phe Pro Pro Thr Ile
            370                 375                 380

Arg Lys Ile Asp Ala Ala Val Ser Asp Lys Glu Lys Lys Thr Tyr
385                 390                 395                 400

Phe Phe Ala Ala Asp Lys Tyr Trp Arg Phe Asp Glu Asn Ser Gln Ser
                    405                 410                 415

Met Glu Gln Gly Phe Pro Arg Leu Ile Ala Asp Asp Phe Pro Gly Val
            420                 425                 430

Glu Pro Lys Val Asp Ala Val Leu Gln Ala Phe Gly Phe Phe Tyr Phe
            435                 440                 445

Phe Ser Gly Ser Ser Gln Phe Glu Phe Asp Pro Asn Ala Arg Met Val
            450                 455                 460

Thr His Ile Leu Lys Ser Asn Ser Trp Leu His Cys
465                 470                 475

(2) INFORMATION FOR SEQ ID NO: 22:

(i) SEQUENCE CHARACTERISTICS:
        (A) LENGTH: 488 amino acids
        (B) TYPE: amino acid
        (C) STRANDEDNESS: single
        (D) TOPOLOGY: linear (xi) SEQUENCE DESCRIPTION: SEQ ID NO: 22:

Met Ala Pro Ala Ala Trp Leu Arg Ser Ala Ala Ala Arg Ala Leu Leu
1               5                   10                  15

Pro Pro Met Leu Leu Leu Leu Gln Pro Pro Pro Leu Leu Ala Arg
            20                  25                  30

Ala Leu Pro Pro Asp Val His His Leu His Ala Glu Arg Arg Gly Pro
            35                  40                  45

Gln Pro Trp His Ala Ala Leu Pro Ser Ser Pro Ala Pro Ala Pro Ala
50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg Phe Val Leu Ser Gly Gly Arg Trp Glu Lys Thr Asp Leu Thr Tyr
                100                 105                 110

Arg Ile Leu Arg Phe Pro Trp Gln Leu Val Gln Glu Gln Val Arg Gln
                115                 120                 125

Thr Met Ala Glu Ala Leu Lys Val Trp Ser Asp Val Thr Pro Leu Thr
130                 135                 140

Phe Thr Glu Val His Glu Gly Arg Ala Asp Ile Met Ile Asp Phe Ala
145                 150                 155                 160

Arg Tyr Trp Asp Gly Asp Asp Leu Pro Phe Asp Gly Pro Gly Gly Ile
                165                 170                 175

Leu Ala His Ala Phe Phe Pro Lys Thr His Arg Glu Gly Asp Val His
                180                 185                 190

Phe Asp Tyr Asp Glu Thr Trp Thr Ile Gly Asp Asp Gln Gly Thr Asp
            195                 200                 205

Leu Leu Gln Val Ala Ala His Glu Phe Gly His Val Leu Gly Leu Gln
            210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                245                 250                 255
```

-continued

```
Tyr Gly Gln Pro Trp Pro Thr Val Thr Ser Arg Thr Pro Ala Leu Gly
            260             265             270

Pro Gln Ala Gly Ile Asp Thr Asn Glu Ile Ala Pro Leu Glu Pro Asp
        275             280             285

Ala Pro Pro Asp Ala Cys Glu Ala Ser Phe Asp Ala Val Ser Thr Ile
    290             295             300

Arg Gly Glu Leu Phe Phe Phe Lys Ala Gly Phe Val Trp Arg Leu Arg
305             310             315             320

Gly Gly Gln Leu Gln Pro Gly Tyr Pro Ala Leu Ala Ser Arg His Trp
            325             330             335

Gln Gly Leu Pro Ser Pro Val Asp Ala Ala Phe Glu Asp Ala Gln Gly
            340             345             350

His Ile Trp Phe Phe Gln Gly Ala Gln Tyr Trp Val Tyr Asp Gly Glu
            355             360             365

Lys Pro Val Leu Gly Pro Ala Pro Leu Thr Glu Leu Gly Leu Val Arg
        370             375             380

Phe Pro Val His Ala Ala Leu Val Trp Gly Pro Glu Lys Asn Lys Ile
385             390             395             400

Tyr Phe Phe Arg Gly Arg Asp Tyr Trp Arg Phe His Pro Ser Thr Arg
            405             410             415

Arg Val Asp Ser Pro Val Pro Arg Arg Ala Thr Asp Trp Arg Gly Val
            420             425             430

Pro Ser Glu Ile Asp Ala Ala Phe Gln Asp Ala Asp Gly Tyr Ala Tyr
            435             440             445

Phe Leu Arg Gly Arg Leu Tyr Trp Lys Phe Asp Pro Val Lys Val Lys
        450             455             460

Ala Leu Glu Gly Phe Pro Arg Leu Val Gly Pro Asp Phe Phe Gly Cys
465             470             475             480

Ala Glu Pro Ala Asn Thr Phe Leu
                485
```